(12) United States Patent
Raman et al.

(10) Patent No.: US 9,890,045 B2
(45) Date of Patent: Feb. 13, 2018

(54) PROCESS FOR SIMULTANEOUS PRODUCTION OF CARBON NANOTUBE AND A PRODUCT GAS FROM CRUDE OIL AND ITS PRODUCTS

(71) Applicant: Indian Oil Corporation Limited, Bandra (East), Mumbai (IN)

(72) Inventors: Naduhatty Selai Raman, Faridabad (IN); Palvannan Mohanasundaram, Faridabad (IN); Narayanam Seshubabu, Faridabad (IN); Jayaraj Christopher, Faridabad (IN); Brijesh Kumar, Faridabad (IN); Anurag Ateet Gupta, Faridabad (IN); Biswapriya Das, Faridabad (IN); Ravinder Kumar Malhotra, Faridabad (IN)

(73) Assignee: INDIAN OIL CORPORATION LIMITED, Bandra (East) (IN)

( * ) Notice: Subject to any disclaimer, the term of this patent is extended or adjusted under 35 U.S.C. 154(b) by 0 days.

(21) Appl. No.: 15/105,563

(22) PCT Filed: Dec. 29, 2014

(86) PCT No.: PCT/IB2014/067383
§ 371 (c)(1),
(2) Date: Jun. 17, 2016

(87) PCT Pub. No.: WO2015/101917
PCT Pub. Date: Jul. 9, 2015

(65) Prior Publication Data
US 2016/0318764 A1 Nov. 3, 2016

(30) Foreign Application Priority Data
Dec. 30, 2013 (IN) .......................... 4116/MUM/2013

(51) Int. Cl.
*C01B 31/02* (2006.01)
*C07C 4/06* (2006.01)
(Continued)

(52) U.S. Cl.
CPC .......... *C01B 31/0233* (2013.01); *B82Y 30/00* (2013.01); *C01B 3/26* (2013.01);
(Continued)

(58) Field of Classification Search
CPC ........ B01J 21/04; C01B 31/0233; C01B 3/26; C01B 2203/0277; C01B 2203/1047;
(Continued)

(56) References Cited

U.S. PATENT DOCUMENTS

2005/0042162 A1* 2/2005 Resasco ................. B01J 8/0055
423/447.3
2008/0223851 A1* 9/2008 Biris ...................... B01J 8/0015
219/634
(Continued)

FOREIGN PATENT DOCUMENTS

EP 2011907 1/2009
WO WO 2012/068781 5/2012
WO WO 2013/081499 6/2013

OTHER PUBLICATIONS

Cheng, et al., Large-scale and low-cost synthesis of single-walled carbon nanotubes by the catalytic pyrolysis of hydrocarbons, Applied Physics Letters 1998; 72(25): 3282-3284.*
(Continued)

*Primary Examiner* — Daniel C McCracken
(74) *Attorney, Agent, or Firm* — Workman Nydegger

(57) ABSTRACT

The present invention is directed to a process for the simultaneous production of carbon nanotubes and product gas comprising hydrogen and lighter hydrocarbons, from a liquid hydrocarbon comprising feeding a liquid hydrocarbon
(Continued)

Figure 1:
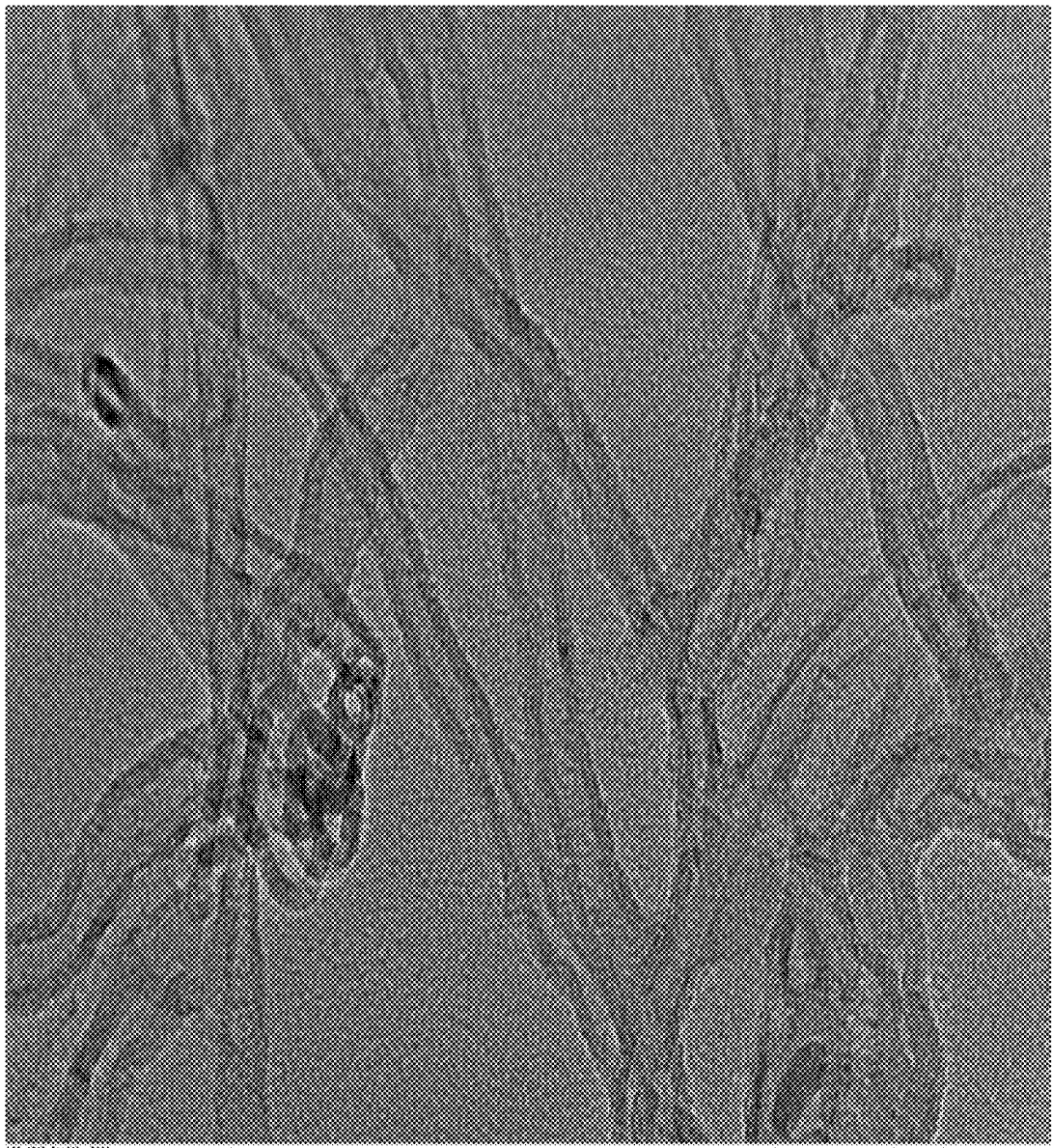

in a reactor; and converting the liquid hydrocarbon with a catalyst for simultaneous production of the carbon nanotubes, hydrogen and lighter hydrocarbons, wherein the liquid hydrocarbon comprises petroleum crude oil, its products, or mixtures thereof.

20 Claims, 22 Drawing Sheets

(51) Int. Cl.
| | |
|---|---|
| *C01B 3/26* | (2006.01) |
| *B82Y 30/00* | (2011.01) |
| *D01F 9/12* | (2006.01) |
| *D01F 9/127* | (2006.01) |
| *C01B 32/162* | (2017.01) |
| *C01B 32/164* | (2017.01) |
| *C01B 32/166* | (2017.01) |
| *B82Y 40/00* | (2011.01) |
| *B82Y 35/00* | (2011.01) |

(52) U.S. Cl.
CPC .......... C01B 32/162 (2017.08); C01B 32/164 (2017.08); C01B 32/166 (2017.08); C07C 4/06 (2013.01); D01F 9/12 (2013.01); D01F 9/127 (2013.01); *B82Y 35/00* (2013.01); *B82Y 40/00* (2013.01); *C01B 2202/36* (2013.01); *C01B 2203/0277* (2013.01); *C01B 2203/1047* (2013.01); *C01B 2203/1052* (2013.01); *C01B 2203/1058* (2013.01); *C01B 2203/1082* (2013.01); *C01B 2203/1094* (2013.01); *C07C 2523/755* (2013.01); *C07C 2523/881* (2013.01); *Y10S 977/742* (2013.01); *Y10S 977/842* (2013.01)

(58) Field of Classification Search
CPC . C01B 2202/36; C01B 32/162; C01B 32/164; C01B 32/166; C07C 4/06; D01F 9/12; D01F 9/127; B82Y 40/00; B82Y 35/00; B82Y 30/00
USPC ........................................................ 423/447.3
See application file for complete search history.

(56) References Cited

U.S. PATENT DOCUMENTS

| | | | |
|---|---|---|---|
| 2012/0129490 A1* | 5/2012 | Sharma | H04L 12/1414 455/406 |
| 2012/0219490 A1* | 8/2012 | Noda | B01J 21/04 423/447.3 |

OTHER PUBLICATIONS

PCT/IB2014/067383, May 4, 2015, International Search Report and Written Opinion.

* cited by examiner

PROCESS FOR SIMULTANEOUS PRODUCTION OF CARBON NANOTUBE AND A PRODUCT GAS FROM CRUDE OIL AND ITS PRODUCTS

FIELD OF THE INVENTION

The present invention relates to a process for simultaneous production of carbon nanotubes, and a product gas comprising hydrogen and lighter hydrocarbons from liquid hydrocarbons from petroleum crude oil and its products employing catalytic conversion at elevated temperatures.

BACKGROUND OF THE INVENTION

In recent years carbon nanotubes have attracted a particular interest due to their unique morphology, and are therefore used widely in various applications due to their versatile mechanical and electrical properties. There is growing application of carbon nanotubes in synthesis of products such as polymer composites, conducting polymers, protecting wares, light weight sports goods, electrodes in batteries etc. Carbon nanotubes are formed by rolling of graphene sheet with $sp^2$ carbon into seamless cylinders of nanosize dimensions. The physio-chemical properties of these carbon nanotubes depend on the structural morphology of the nanotubes.

Carbon nanotubes are classified into three categories viz. single walled, double walled and multi-walled carbon nanotubes depending on the shape and dimension of the tube. Each carbon nanotube type has unique characteristic properties due to their structural morphology. In general, carbon nanotubes with diameter as high as 5 nm are considered as single walled and types with diameter 6-100 nm diameter is considered as multiwalled nanotubes, whose inter-layer spacing is close to 0.34 nm.

U.S. Pat. No. 8,398,894 B2 discloses the method of producing carbon nanotube having desired apparent density by catalytic decomposition of gaseous mixture of ethylene and hydrogen at 650° C. using catalysts prepared by co-precipitation method.

US 20090140215 A1 patent describes the production of carbon nanotubes of 3-150 nm diameter by decomposition of ethylene as feedstock at 6500 C in the presence of H2 and Ar on supported metal catalyst which comprises mainly Co, Mn and Mo.

US2012077031 (A1) discloses the catalyst composition for the synthesis of thin multi walled carbon nanotubes having diameter of 5-20 nm using the gaseous mixture of hydrogen and carbon source selected either from saturated or unsaturated hydrocarbon having 1 to 4 carbon atoms in the temperature range of 500° C. to 900° C. The catalysts disclosed comprises the Co as main active metal along with promoters selected from Ni, Cr, Mn, Mo, W, Pb, Ti, Sn, or Cu, its oxide, or its derivative on inactive MgO support carrier using co-precipitation method under the controlled pH conditions.

EP 1 318 102 A1 describes the production of single walled/multi walled carbon nanotubes from acetylene, ethylene, butane, propane, ethane, methane using catalytic chemical vapor deposition.

CN 1443708 discloses the method of preparing the multi walled carbon nanotubes synthesis from methane feedstock using single metal and with promoter combination.

U.S. Pat. No. 8,093,176 B2 discloses the process for continuous production of catalysts for the formation of carbon nanotubes. Co, Mn and Mo are used as catalysts in different metal ratios without any support material. The hydrocarbon feedstock with carbon number C1-C4 of aliphatic and olefinic compounds used.

US 20120219490A1 describes the simultaneous production of carbon nanotubes and hydrogen from gaseous carbon source feedstock constituent of carbon and hydrogen atoms. The method deals the production of single walled carbon nanotubes and hydrogen from gaseous feedstock in the presence of vaporized metal catalyst.

U.S. Pat. No. 6,413,487 patent describes the method and apparatus for producing carbon nanotubes. The invention mainly describes the synthesis of carbon nanotubes either from CO, CH4, C2H2, C2H4 and mixtures by using Group VIII metal catalysts.

WO 2007033438 discloses the catalyst system for a multi-walled carbon nanotube production process using natural gas and mixture of methane and olefin gas.

WO 2001085612 A2 describes the process for preparing carbon nanotubes using methane, ethane, acetylene and carbon monoxide in the presence of Ni—Co catalysts.

In the above prior art, the feedstock used are gaseous hydrocarbon having carbon number in the range C1 to C4 with an objective of producing carbon nanotube. However, the above prior art have not disclosed on use of liquid hydrocarbon mixture say, crude oil or its products as feedstock with an objective of producing carbon nanotube along with mixture of hydrogen and methane, which can be used directly as a transportation fuel.

U.S. Pat. No. 6,730,284 describes the method for producing carbonaceous articles by chemical vapor deposition, wherein hydrocarbon and oxygen containing hydrocarbons and aromatic hydrocarbon are used as feed stocks by using Group I B metals and second metal selected from the group of Fe, Ni, Co, Zn and mixtures in the range of 100-11000 C operating temperature.

U.S. Pat. No. 7,160,531 disclose the process for the continuous production of aligned carbon nanotubes. The invention features the dispersion of organo metallic catalyst with liquid hydrocarbon to form a feed solution and volatilizing the feed solution. The hydrocarbon liquid contains organo metal catalyst of at least 0.5 wt. % in the dispersed state. In the disclosure, liquid organo metallic catalyst has been employed.

It is clear from the above prior art that the disclosures are related to the synthesis of carbon nanotubes from various carbonaceous raw materials particularly single molecule hydrocarbons including gases and liquid hydrocarbon as feedstock. The above prior arts disclose use of single molecules gaseous/liquid feedstock or mixture thereof for the production of carbon nanotube. Such a process is usually expensive and there is a need to find alternative methods which are more economic to produce carbon nanotubes (CNT) on a commercial scale.

SUMMARY OF THE INVENTION

The present invention relates to an economic and commercially viable process for the simultaneous production of carbon nanotubes, hydrogen and lighter hydrocarbons.

In one aspect, the present invention provides a process for the simultaneous production of carbon nanotubes and a product gas comprising hydrogen and lighter hydrocarbons from a liquid hydrocarbon comprising feeding a liquid hydrocarbon in a reactor; and converting the liquid hydrocarbon in presence of catalyst for simultaneous production of the carbon nanotubes, product gas comprising hydrogen and lighter hydrocarbons, wherein the liquid hydrocarbon comprises petroleum crude oil or its products and mixture thereof.

Another aspect of the invention relates to a process for the production of carbon nanotubes comprising feeding a liquid hydrocarbon in a reactor; and converting the liquid hydrocarbon with a catalyst for production of the carbon nanotubes, wherein the liquid hydrocarbon is selected from a petroleum crude oil, its products and mixtures thereof.

The catalyst used in the process is either bulk or supported active metal catalysts which can be used with or without promoter. The active metal is selected from Group VIII metals and the promoter is selected from Group IB, VIB, VIIB, VIII metals and mixture thereof. The active metal may be selected from the group comprising of Fe, Co, Ni and the promoter may be selected from the group comprising of Fe, Ni, Co, Cu, Mo, W, Cr or Mn. The active metal may be supported on a metal oxide support and the metal oxide is selected from the group comprising of alumina, silica, silica-alumina, zeolite, titania, magnesia, clay materials and carbon materials.

The ratio of active metal to metal oxide support is in the range of 1 to 100 wt. %/wt. %, preferably in the range of 5-40 wt. %/wt. % and the ratio of active metal to promoter is in the range of 0 to 20 wt. %/wt. %, preferably in the range of 1-10 wt. %/wt. %.

The catalytic reactor may be operated with or without a vibrating function. The reactor may be maintained at a temperature in the range of 300-1200° C., preferably in the range of 500-900° C. The reactor may be maintained at an operating pressure in the range of 1 mbar to 10 mbar, preferably in the range of 1 mbar to 5 mbar. The catalytic conversion is carried out at an elevated temperature in the range of 500-1200° C.

The feeding of the liquid hydrocarbon into the reactor is carried out with the help of a carrier gas. The carrier gas is selected from the group comprising of nitrogen, helium, argon, hydrogen, carbon dioxide, or mixture thereof. The lighter hydrocarbons are C1-C5 gases, preferably methane, ethane, ethylene, propane, propylene, butane, isobutane, 2-butene and pentane. The product gas stream of C1 to C5 hydrocarbons is partially or completely recycled back into the reactor or feed to another reactor.

The carbon nanotube yield in the process of the first aspect ranges from 1 wt. % to 80 wt. %, preferably 20 wt. % to 60 wt. % of the liquid hydrocarbon. The carbon nanotube purity ranges from 70 wt. % to 99.5 wt. %, preferably in the range of 90 wt. % to 98 wt. %. The product gas comprises of hydrogen and lighter hydrocarbons such as C1-C5 hydrocarbons, of which hydrogen gas is in the range of 10 vol. % to 90 vol. % of product gas. The yield of hydrogen is in the range of 1 wt. % to 12 wt. %, preferably 5 wt. % to 10 wt. % of the liquid hydrocarbon.

The carbon nanotube yield in the process of the second aspect ranges from 1 wt. % to 80 wt. %, preferably 20 wt. % to 60 wt. % of the liquid hydrocarbon. The carbon nanotubes are produced with diameter of 1 to 100 nm, preferably 1 nm-30 nm. Carbon nanotube purity ranges from 70 wt. % to 99.5 wt. % preferably in the range of 90 wt. % to 98 wt. %. The process also yields a product gas comprising of hydrogen in the range of 10 vol. % to 90 vol. % and methane in the range of 10 vol. % to 90 vol. %. The process also yields hydrogen in the range of 1 wt. % to 12 wt. %, preferably 5 wt. % to 10 wt. % of the liquid hydrocarbon.

BRIEF DESCRIPTION OF ACCOMPANYING DRAWINGS

FIG. 1: Transmission Electron Microscope (TEM) Image of carbon nanotube produced from low sulphur crude oil.

Figure 2:
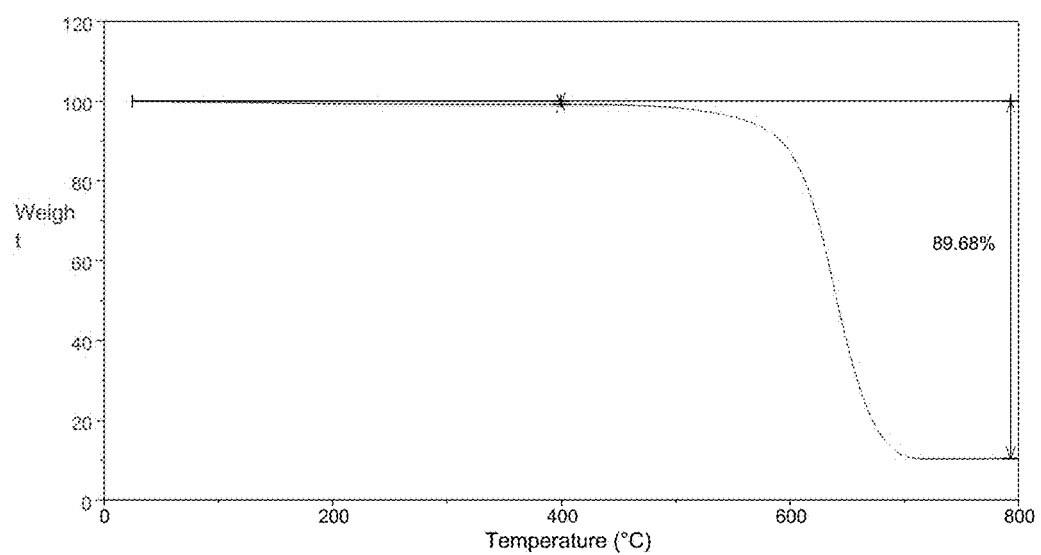

FIG. 2: Thermal Gravimetric Analysis (TGA) of carbon nanotube produced from low sulphur crude oil as feed stock.

Figure 3:
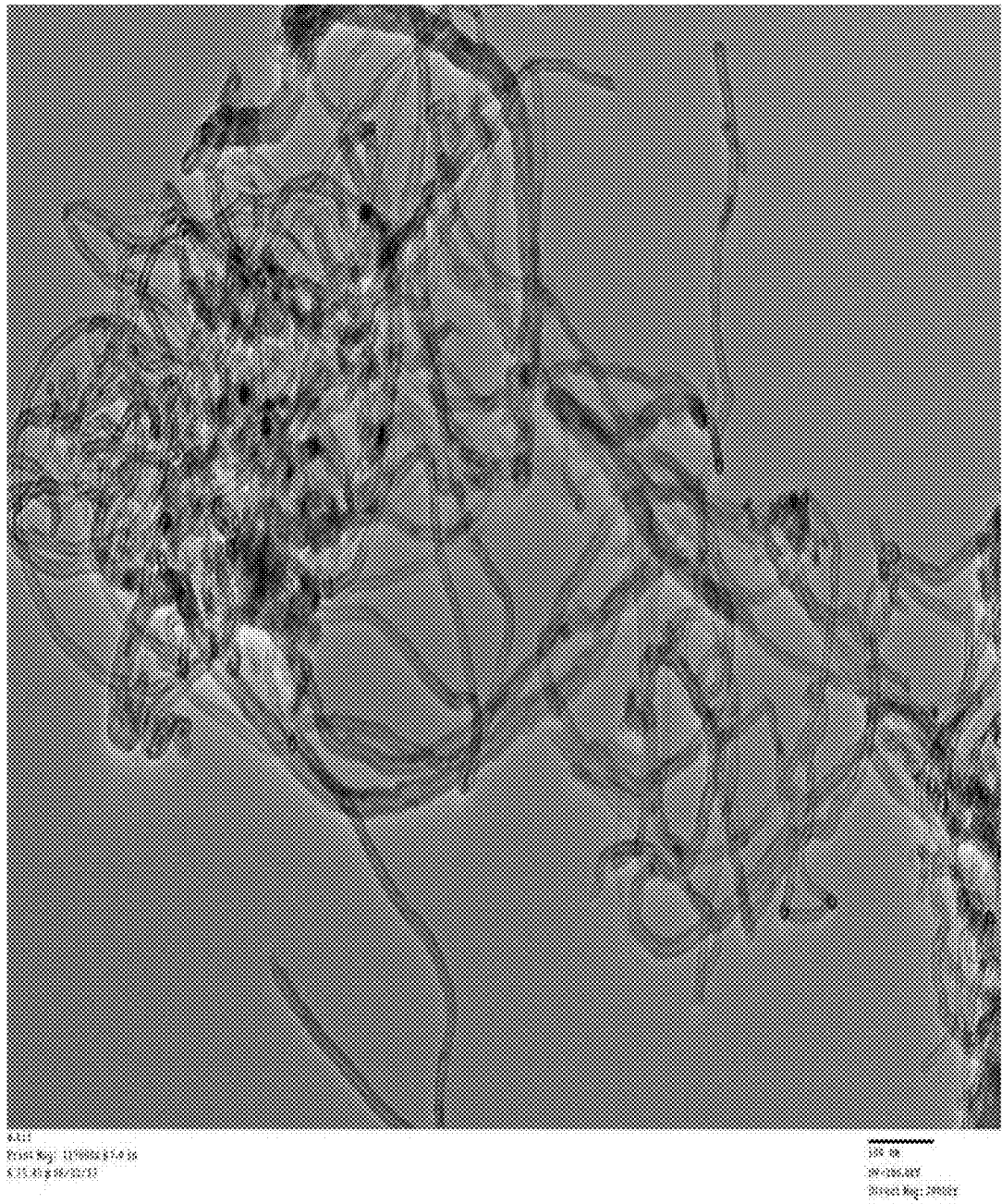

FIG. 3: Transmission Electron Microscope (TEM) image of carbon nanotube produced from high sulphur crude oil.

Figure 4:
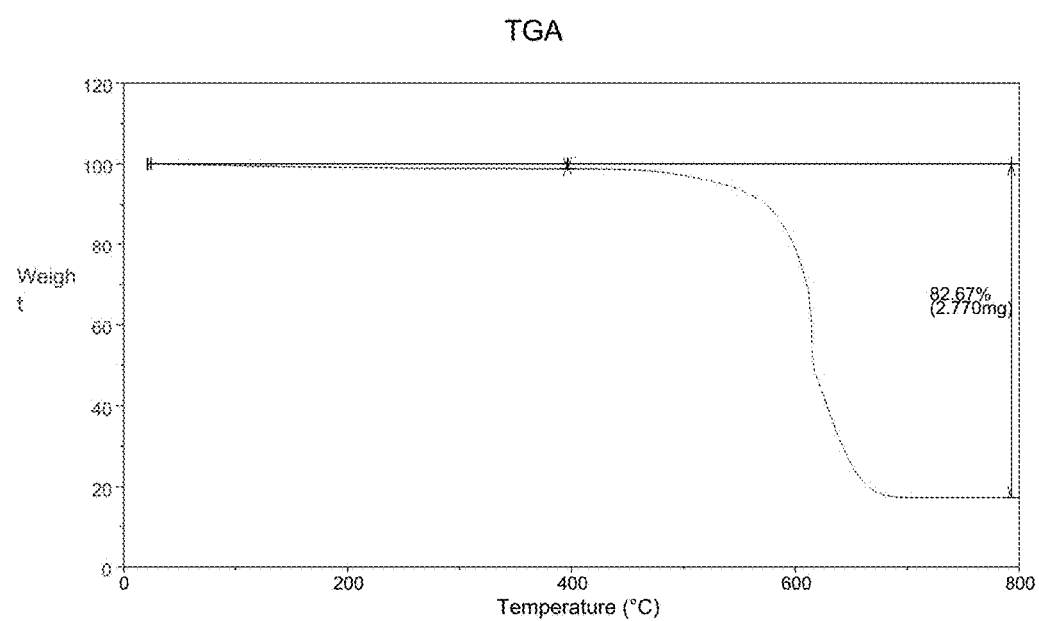

FIG. 4: Thermal Gravimetric Analysis (TGA) of carbon nanotube produced from high sulphur crude oil as feed stock.

Figure 5:
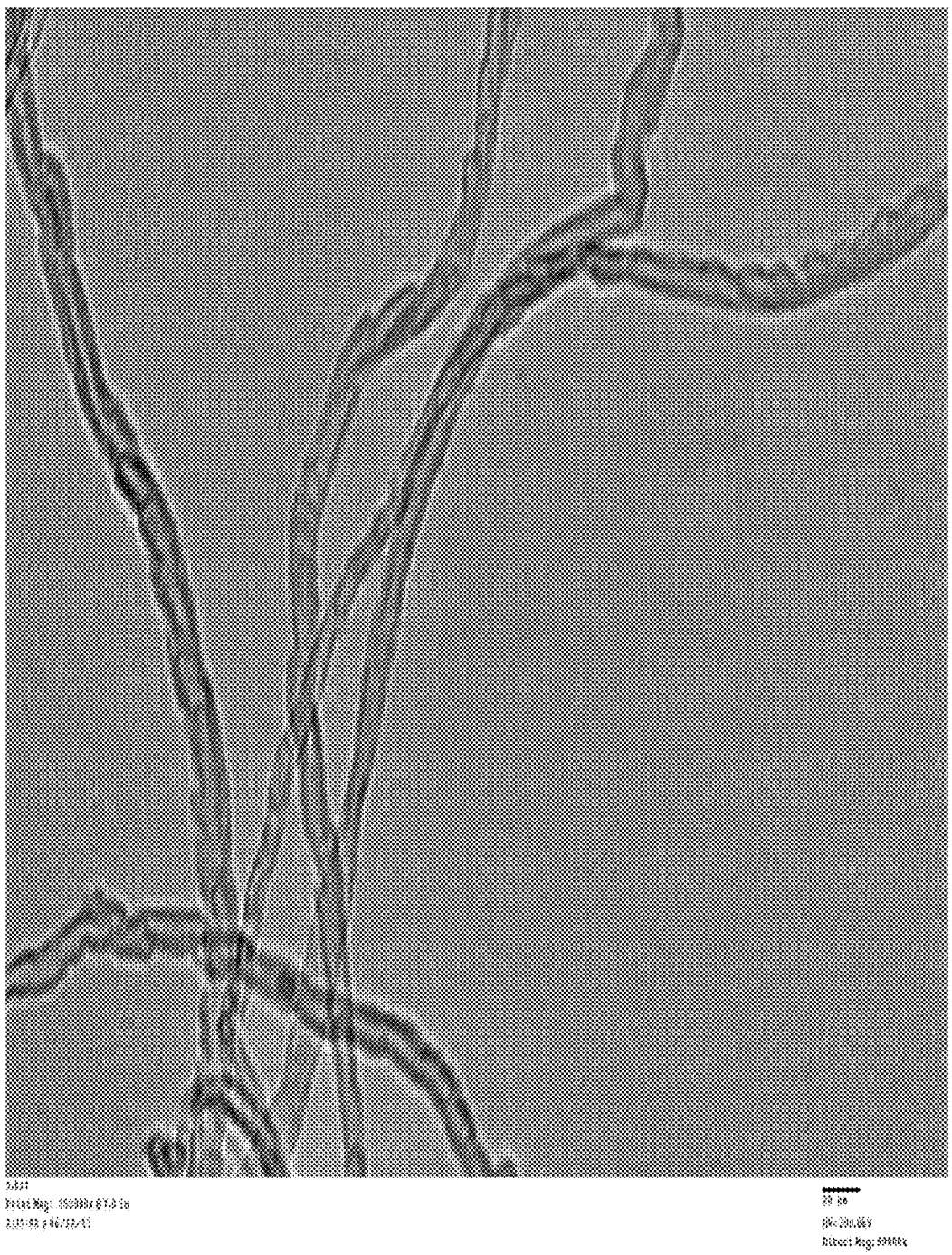

FIG. 5: Transmission Electron Microscope (TEM) Images of carbon nanotube produced from high sulphur crude oil as feed stock at 600° C.

Figure 6:
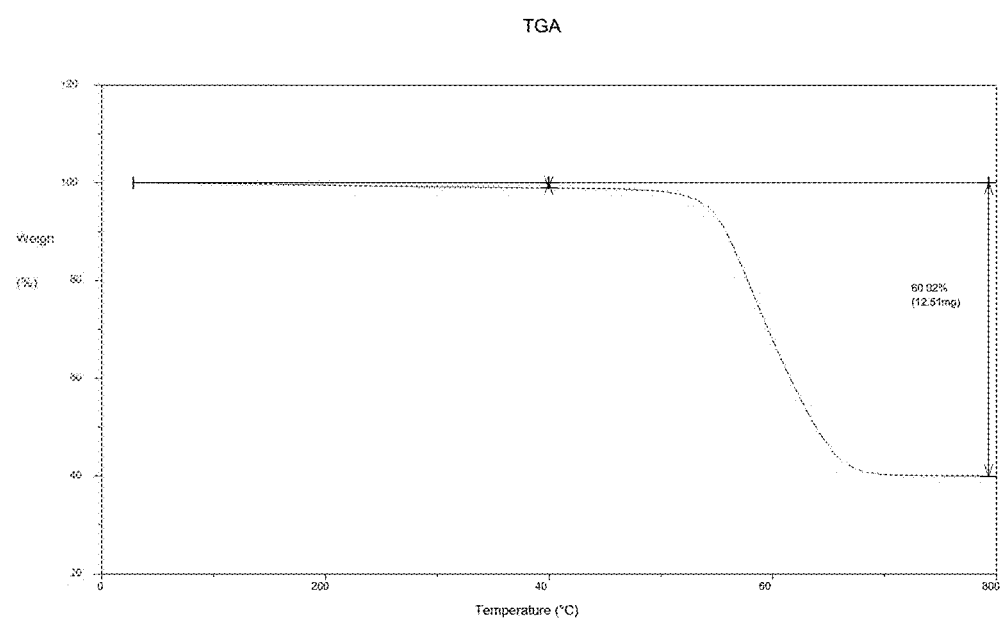

FIG. 6: Thermal Gravimetric Analysis (TGA) of carbon nanotube produced from high sulphur crude oil as feedstock at 600° C.

Figure 7:
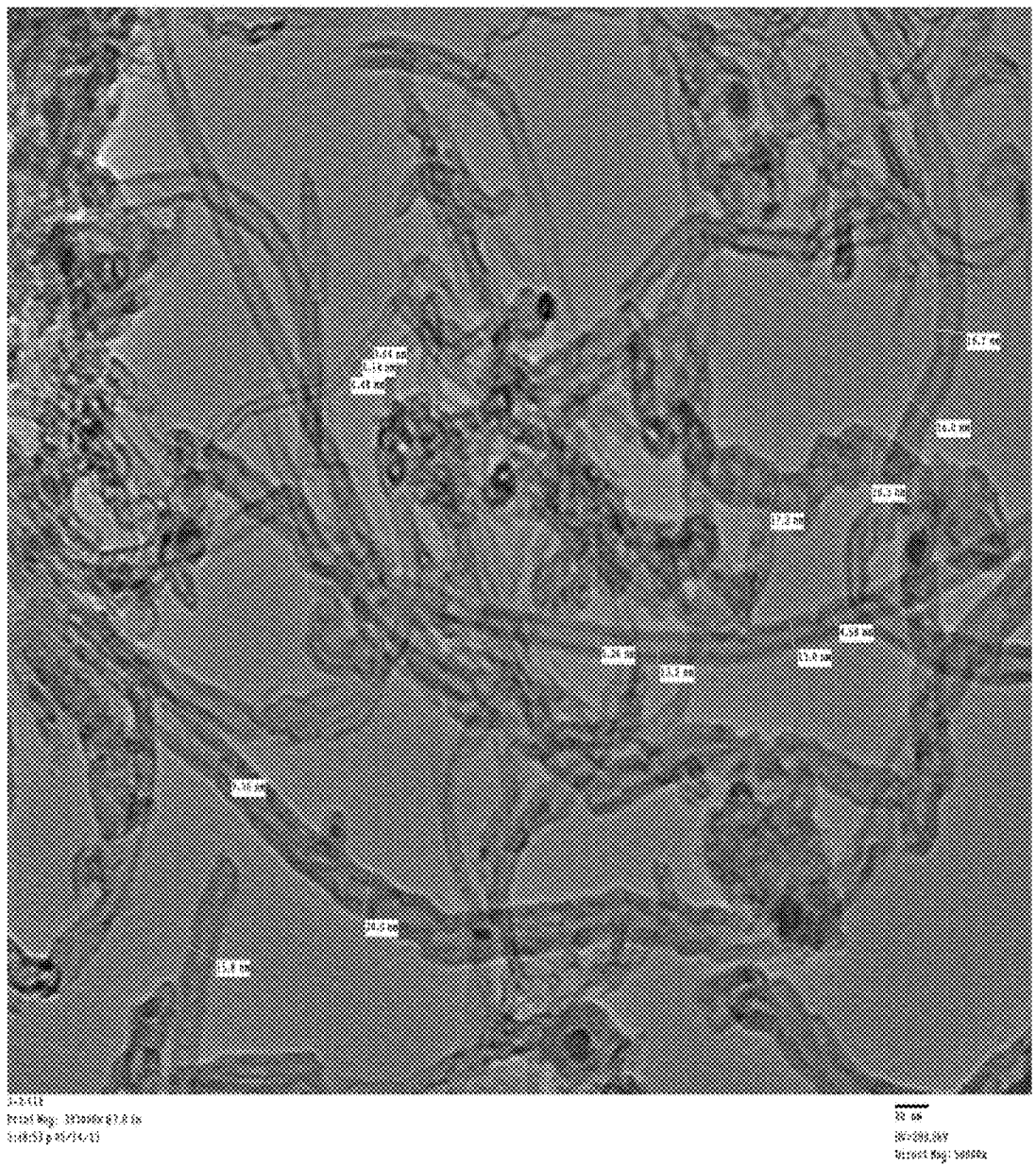

FIG. 7: Transmission Electron Microscope (TEM) Image of carbon nanotubes produced from naphtha feedstock.

Figure 8:
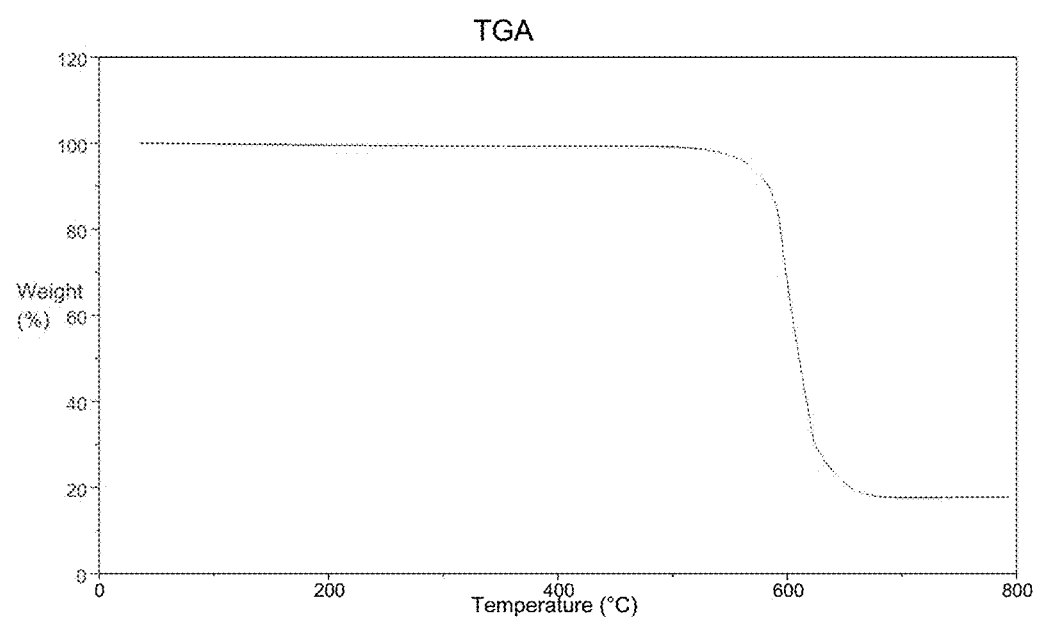

FIG. 8: Thermal Gravimetric Analysis (TGA) of carbon nanotube produced from naphtha as feedstock.

Figure 9:
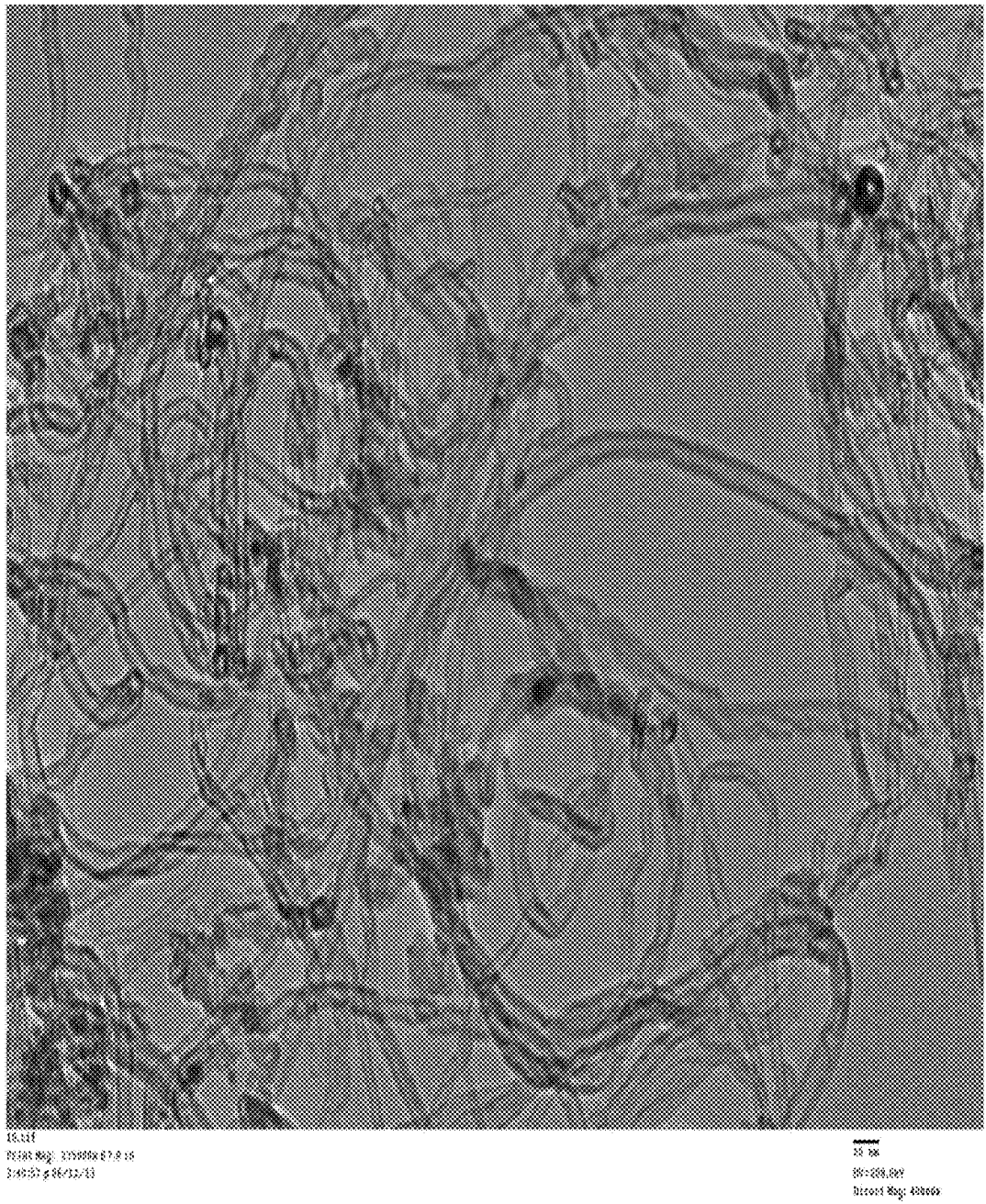

FIG. 9: Transmission Electron Microscope (TEM) Images of carbon nanotubes produced from naphtha feedstock.

Figure 10:
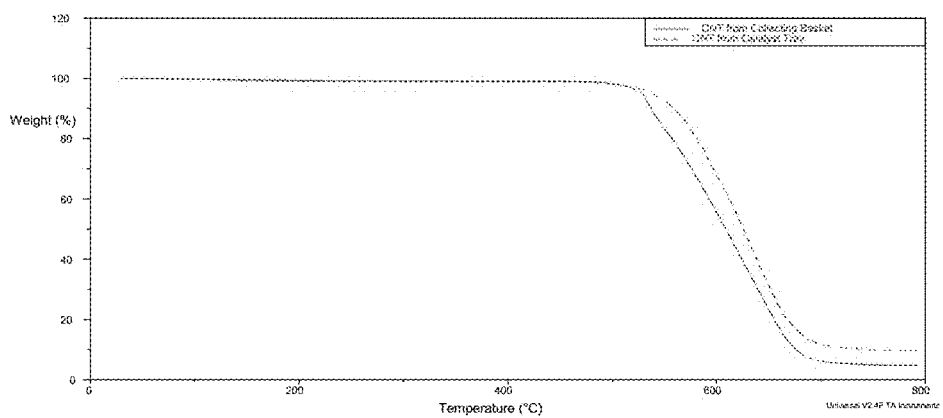

FIG. 10: Thermal Gravimetric Analysis (TGA) of carbon nanotube produced from naphtha feedstock.

Figure 11:
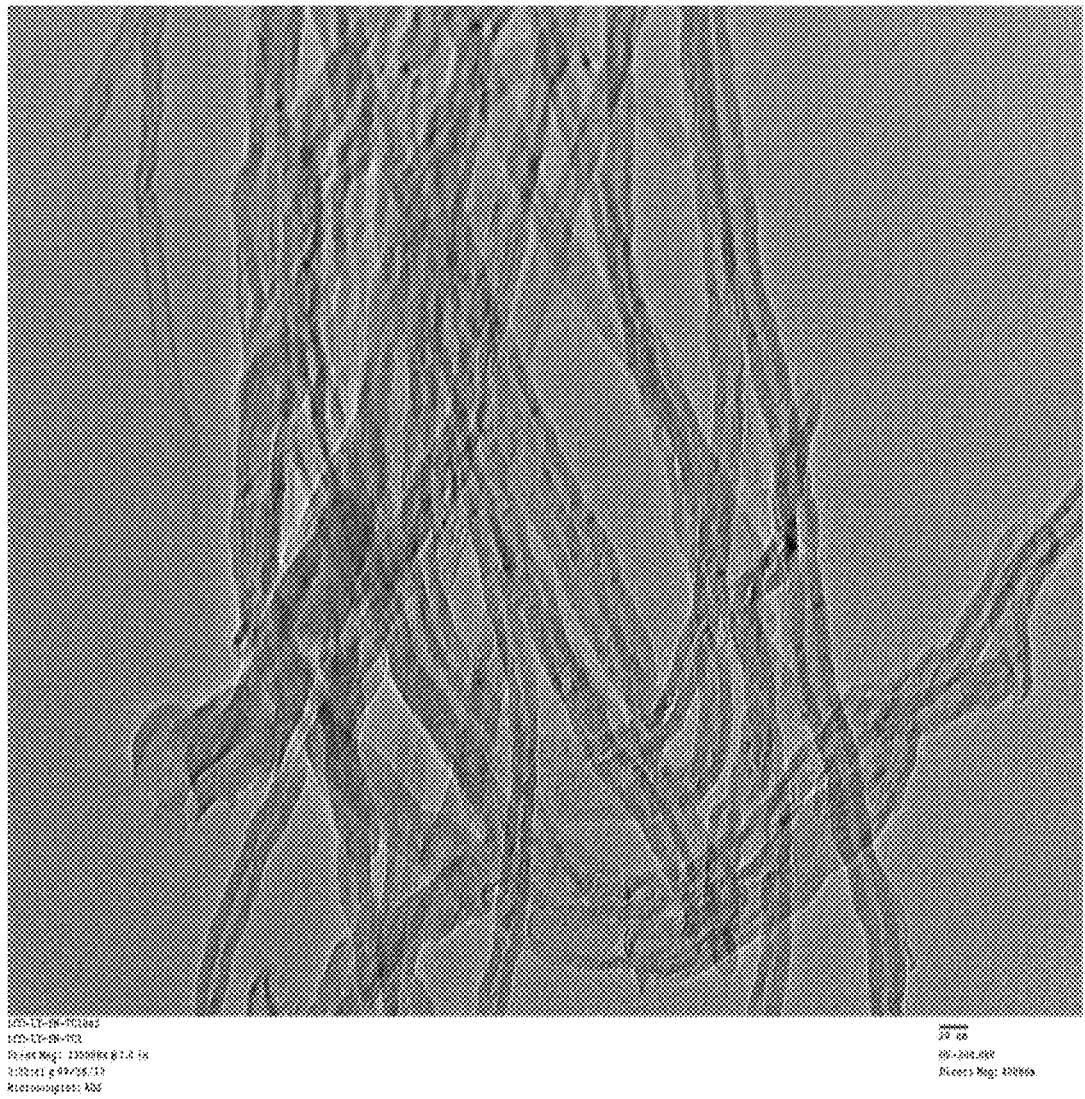

FIG. 11: Transmission Electron Microscope (TEM) Image of carbon nanotube produced from process with vibrator operation FIG. 12: Thermal Gravimetric Analysis (TGA) of carbon nanotube produced from light cycle oil as feedstock.

Figure 13:
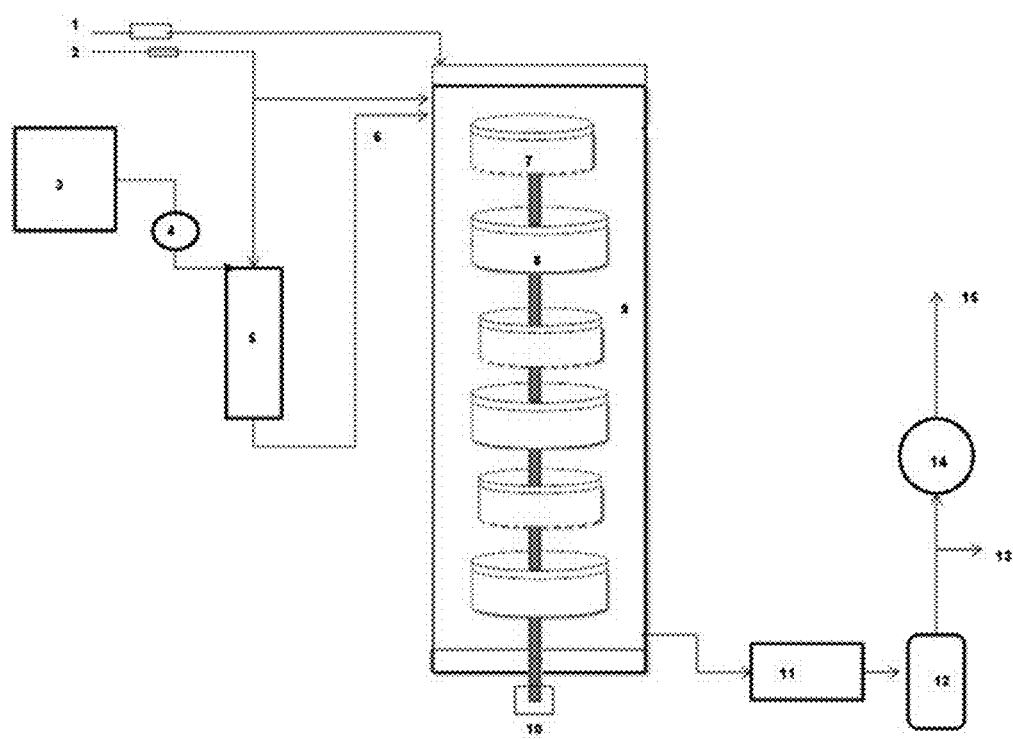

FIG. 13: Schematic diagram of catalytic vibrating reactor.

Figure 14:
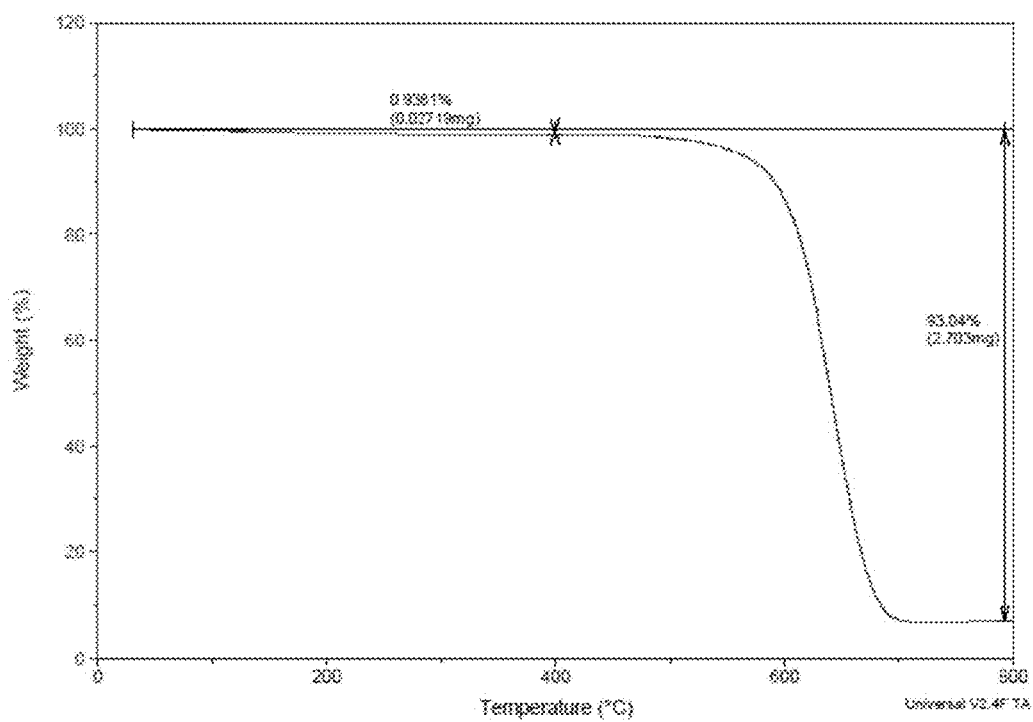

FIG. 14: Thermal Gravimetric Analysis (TGA) of carbon nanotube produced from high sulphur crude oil.

Figure 15:
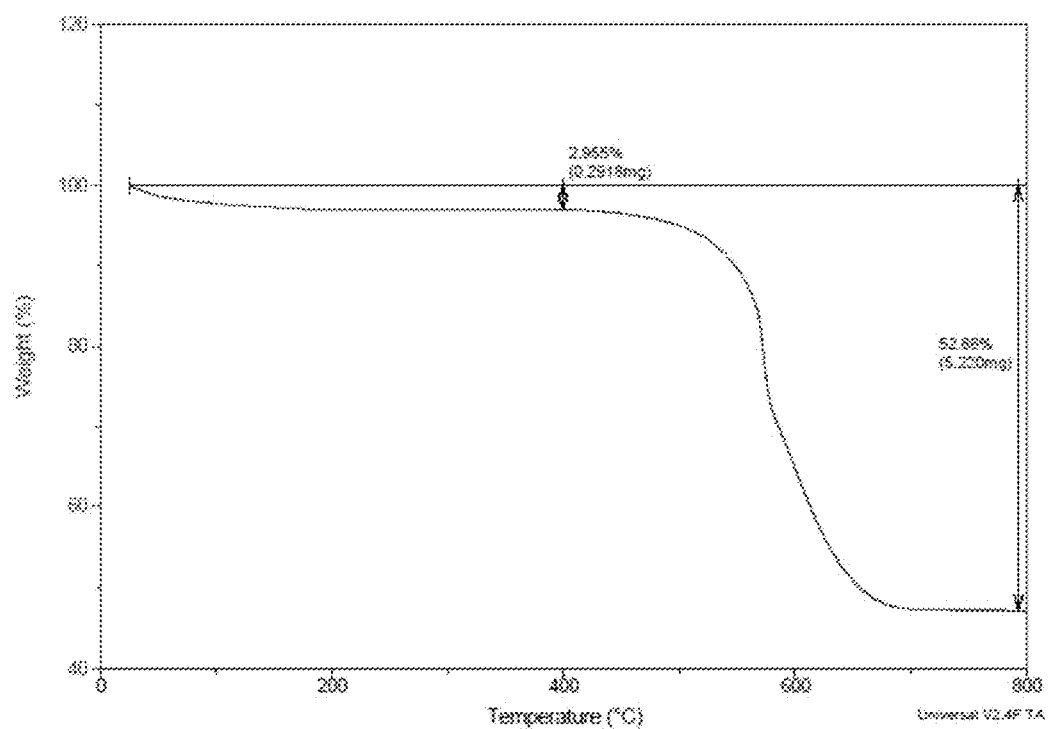

FIG. 15: Thermal Gravimetric Analysis (TGA) of carbon nanotube produced at 500° C.

Figure 16:
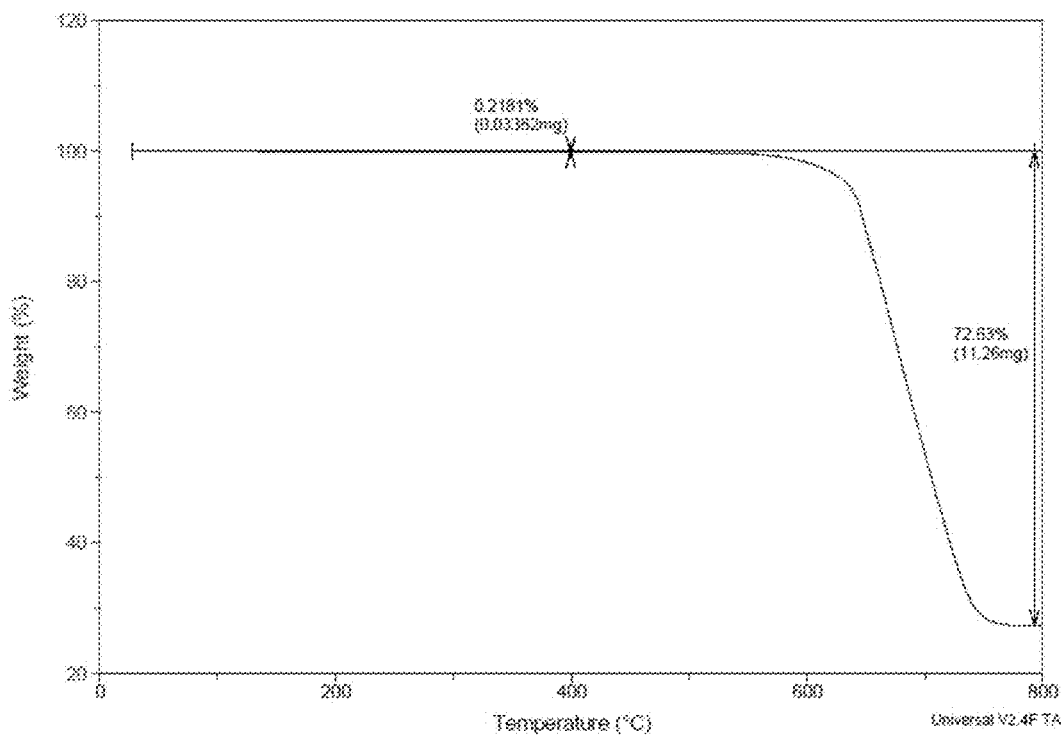

FIG. 16: Thermal Gravimetric Analysis (TGA) of carbon nanotube produced at 600° C.

Figure 17:
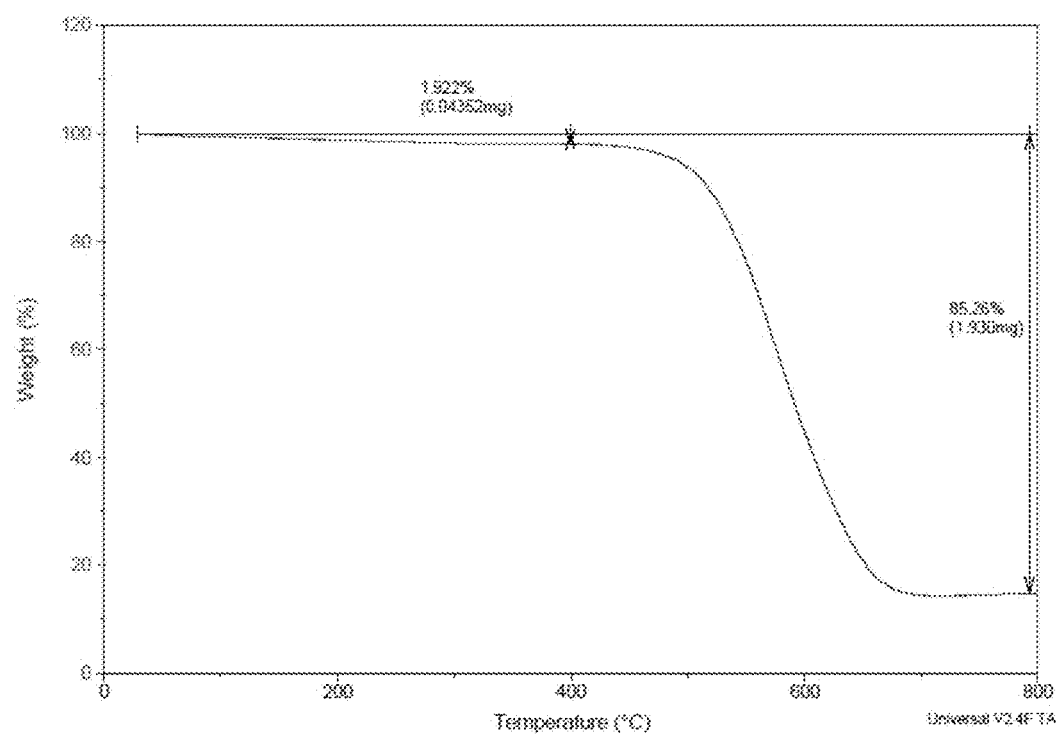

FIG. 17: Thermal Gravimetric Analysis (TGA) of carbon nanotube produced at 700° C. with Ni—Co catalyst.

Figure 18:
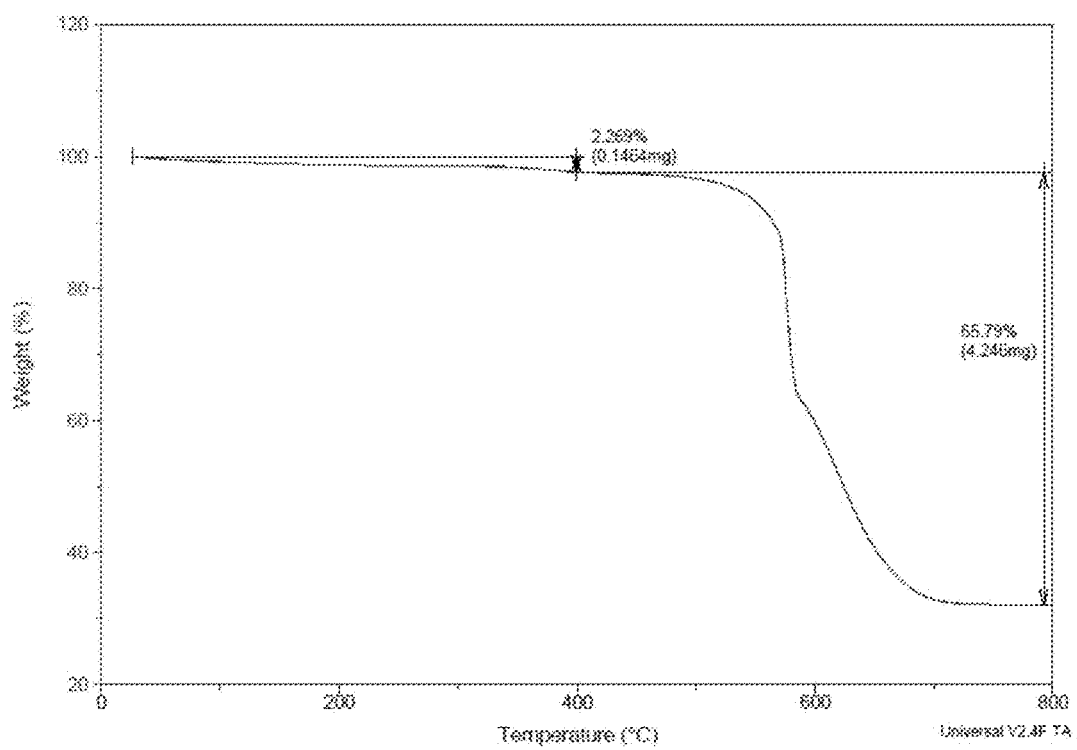

FIG. 18: Thermal Gravimetric Analysis (TGA) of carbon nanotube produced at 500° C. with Ni—Co catalyst.

Figure 19:
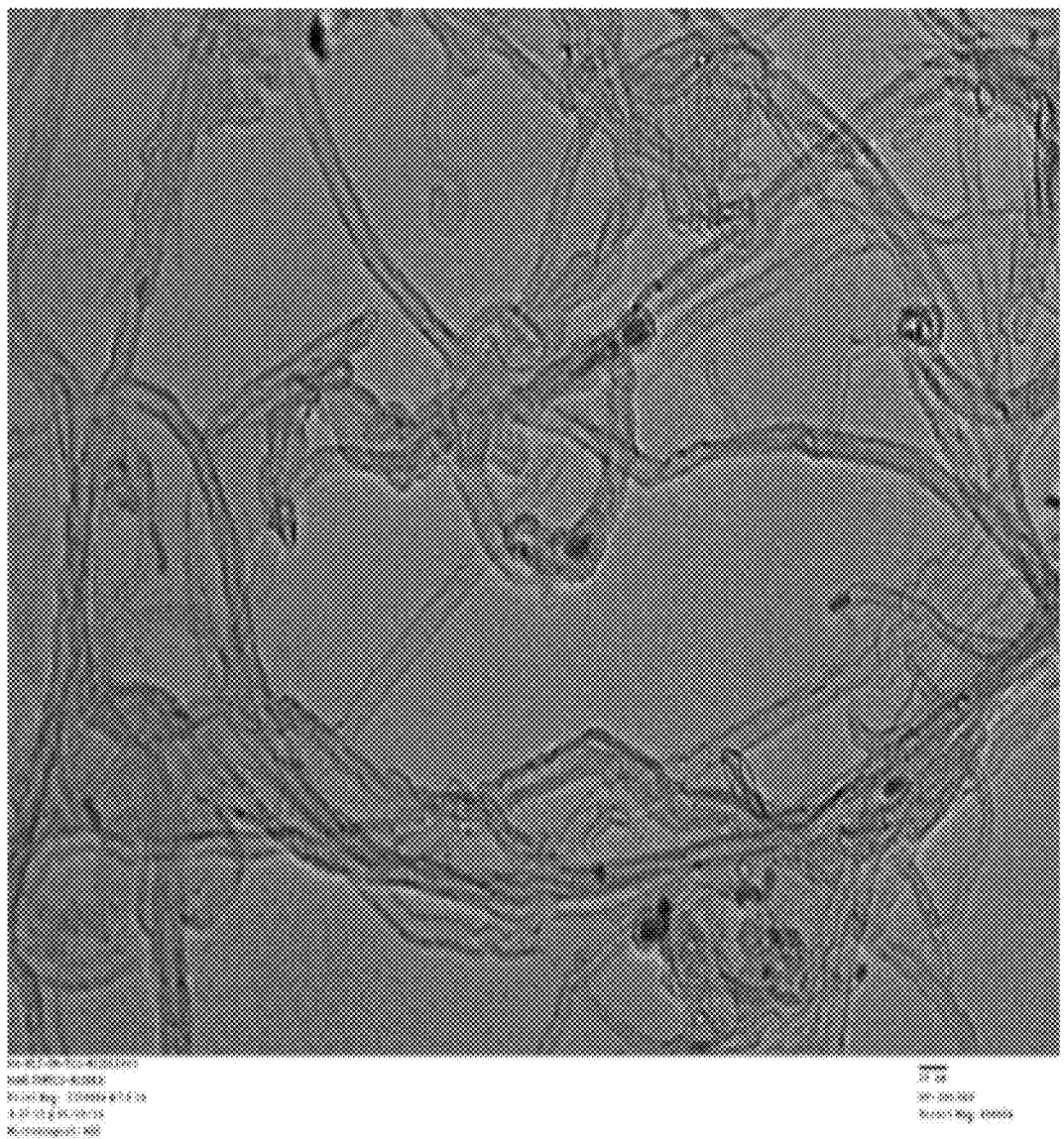

FIG. 19: Transmission Electron Microscope (TEM) images of carbon nanotube from Naphtha using $H_2$ carrier gas.

Figure 20:
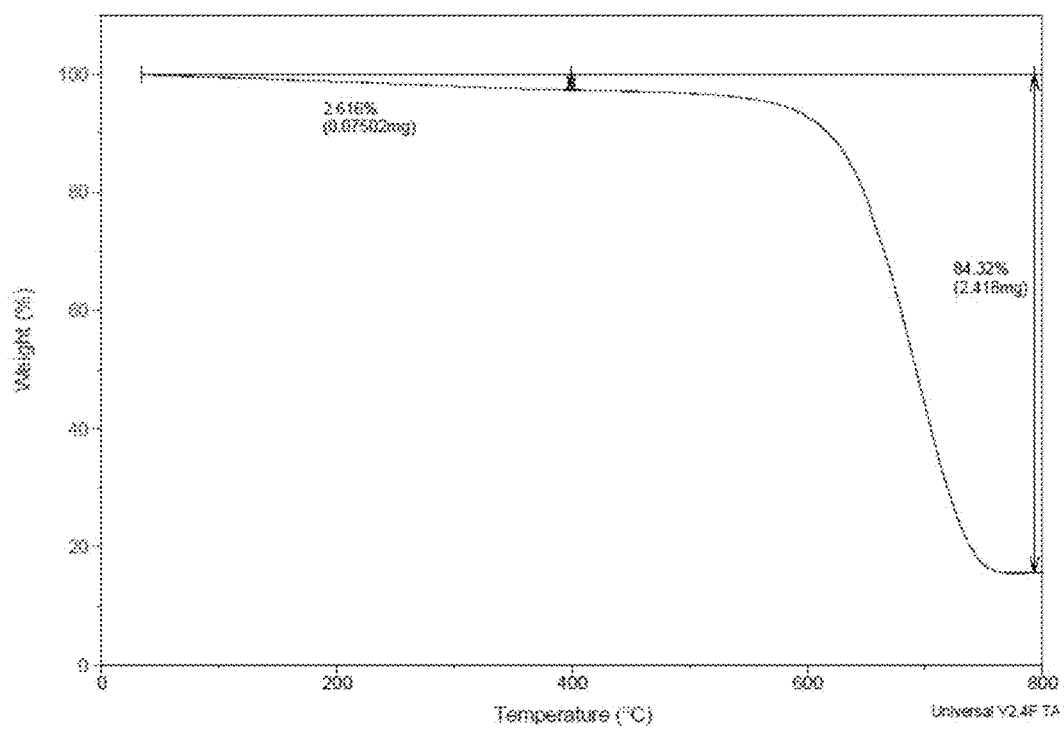

FIG. 20: Thermal Gravimetric Analysis (TGA) of carbon nanotube from Naphtha using $H_2$ carrier gas.

Figure 21:
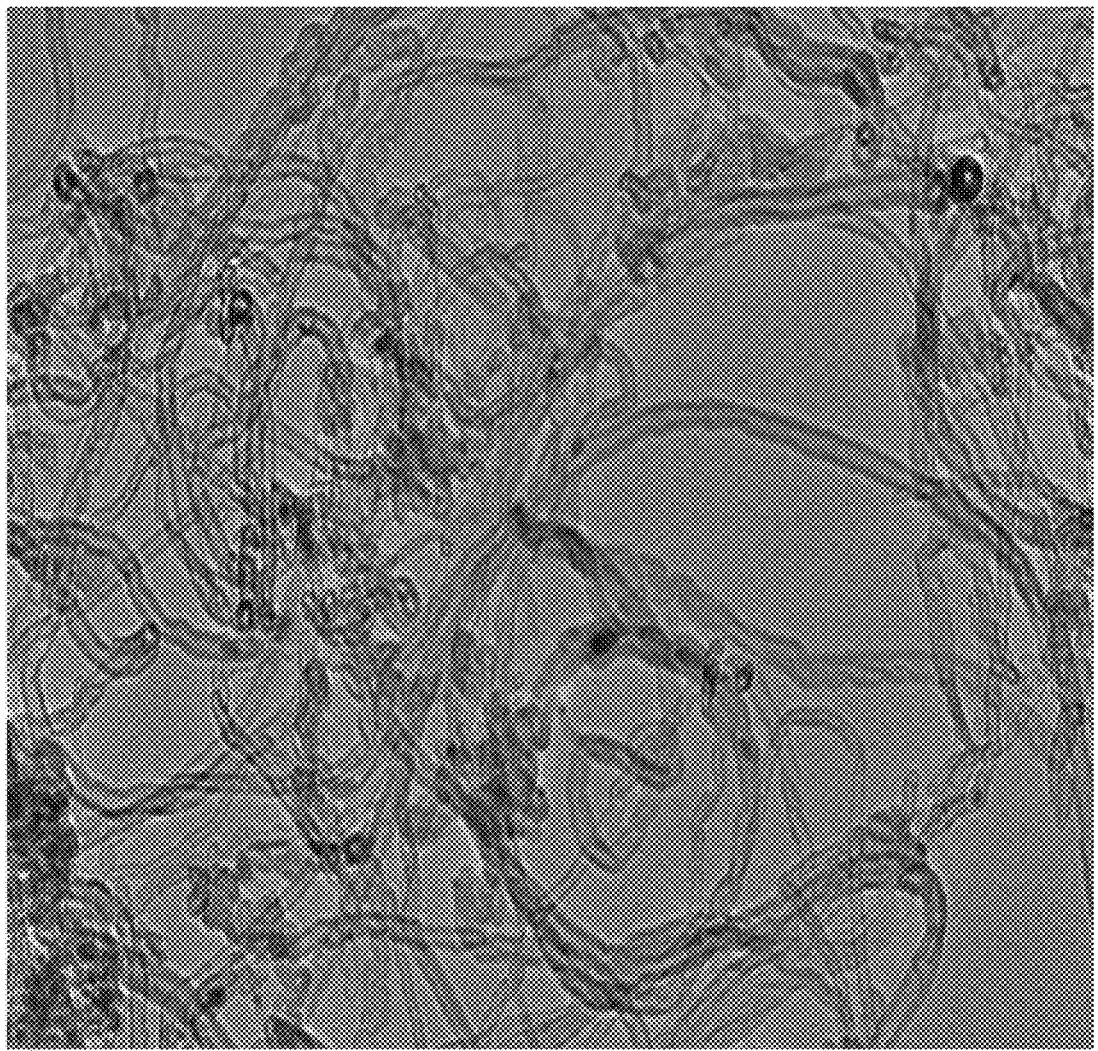

FIG. 21: Transmission Electron Microscope (TEM) images of carbon nanotube from Naphtha at 800° C.

Figure 22:
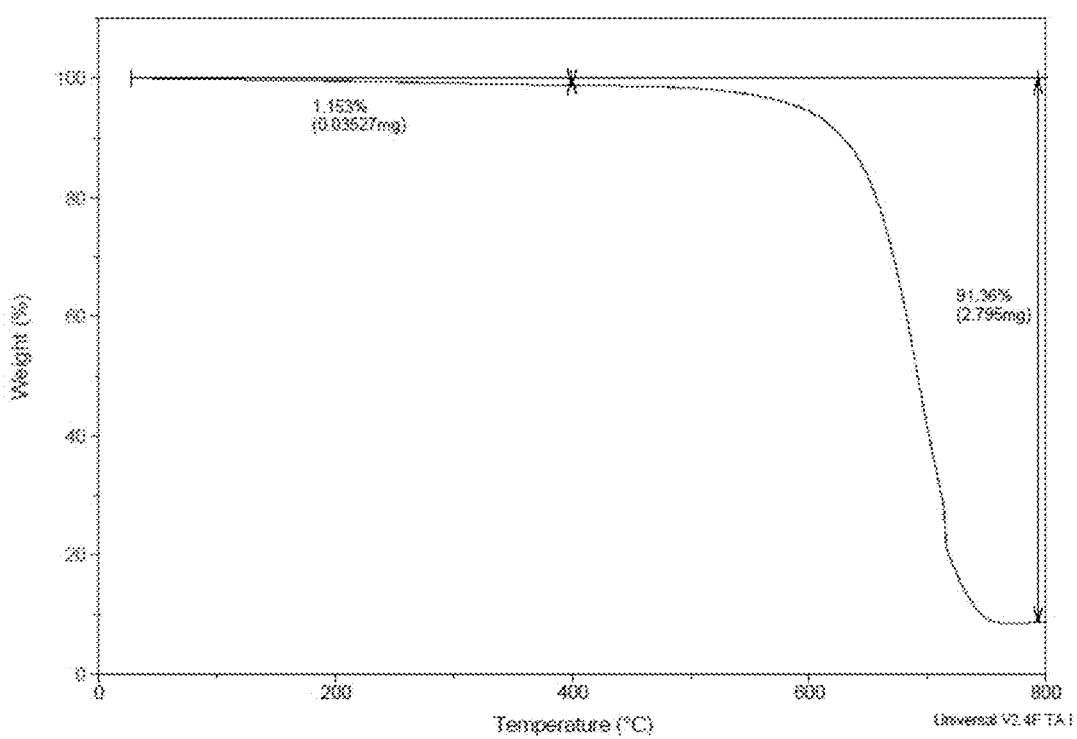

FIG. 22: Thermal Gravimetric Analysis (TGA) of carbon nanotube produced from Naphtha at 800° C.

DETAILED DESCRIPTION OF THE INVENTION

While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternatives falling within the scope of the invention as defined by the appended claims.

The phrase "Bulk active metal catalyst" refers to bulk metal oxide catalysts generally prepared with high amount of metal loading either in presence or absence of support. In general, dispersion of active metal is lower in bulk catalysts since the availability of bare support is lower due to high concentration of metals.

The phrase "Supported active metal catalyst" refers to uniform dispersion of active metals over high surface area supports like Alumina, Magnesia, Silica etc. In these catalysts, active metal loading on the support surface varies from as low as 0.5 wt % to 25 wt % maximum. The dispersion of active metal is higher as compared to bulk metal catalysts.

The term "Promoter" refers to minor amount of metal/non metal element along with active metal component. Promoter is always used in combination with active metal to suppress undesired activity of active metal and render to maintain the longer activity of main metal. In general, promoter typically delays active metal sintering process. At high temperatures, the particles of a finely divided catalyst tend to fuse together and form like cake, which is known as sintering. This reduces the activity of catalyst and therefore steps must be taken to avoid this. To prevent the metal sintering, promoter is usually added during the catalyst synthesis.

The phrase "Intrinsic growth promoter" refers to heterocyclic molecules such as thiophenes which are invariably present in the petroleum feed stock in different proportions. Without being bound by the theory, it is believed that the intrinsic growth promoter molecules react with active metal component of catalyst during the process of decomposition and form metal-heteroatom bond, which is thought to promote the carbon nanotube (CNT) growth.

The phrase "Product gas" refers to the by-product of process of producing CNT, resulted from the hydrocarbon decomposition process, which mainly comprises of hydrogen, methane, and other lighter hydrocarbons of C2-C5 range.

The use of complex mixture of liquid hydrocarbon feedstock has not been disclosed or taught in the prior art as a source for production of carbon nanotubes. More specifically, petroleum crude oil and its products have not been disclosed for the simultaneous production of carbon nanotubes, hydrogen and lighter hydrocarbons.

The present invention discloses a process for simultaneous production of carbon nanotubes, from liquid hydrocarbons preferably from the petroleum crude oil and its products employing catalytic conversion at elevated temperatures, preferably in the range of 500° C. to 1200° C. at the operating pressure of 1 mbar to 10 bar in a batch or continuous reactor. The high temperature is used in the process to facilitate the decomposition of hydrocarbon on the catalyst surface, wherein active phase of (meta) stable metal-carbide bond takes place, which is required for CNT growth process. The use of lower temperature is not recommended while carrying out the process. Lower temperature causes partial decomposition of hydrocarbon on the catalyst surface. Further, yield of CNT at a lower temperature is lower due to inability of metal-carbide formation below 500° C., thereby leading to cracking products.

An aspect of the invention discloses the simultaneous production of hydrogen and lighter hydrocarbons during the production of carbon nanotubes from liquid hydrocarbons employing catalytic conversion at elevated temperatures.

Another aspect of the invention discloses the use of a catalyst composite, either bulk or supported metal catalyst, comprising of an active metal, which is selected from Group VIII metals, a promoter which is selected from Group IB, VIB, VIIB, VIII metals or mixtures thereof along with oxide metal support. Bulk catalysts are low dispersed metal oxide catalysts with metal loading of approximately >50 wt. % (e.g., iron oxide, cobalt oxide, nickel oxide or combination thereof). Bulk metal oxide catalysts are thermally less stable with respect to supported metal catalysts and are prone to sinter at higher temperatures. In contrast thereto, supported catalysts are formed by dispersion of active metals on inert support with metal loading up to 25 wt. %. In supported metal catalysts, active metal is stabilized on the support surface by strong metal-support interaction. The support material provides the surface area and thermal stability of the catalyst.

In one aspect of the present invention, naturally available liquid hydrocarbon mixture namely, petroleum crude oil and its products are used as feedstock which contains saturates, aromatics, resins, asphaltenes, olefins, along with sulphur, nitrogen, oxygen and metals etc. The products of petroleum crude oil used in accordance with this invention include but are not limited to, Naphtha, Light Cycle oil, Decanted Clarified Oil from Fluid Catalytic Cracking, Aromatic Extract, Un Converted Oil (UCO) from hydrocracker bottom, De Asphalted Oil (DAO), Coker Furnace Oil (CFO), Pyrolysis Furnace Oil (PFO), Reduced Crude Oil, Vacuum Gas Oil (VGO) or mixtures thereof.

Naturally available liquid hydrocarbons derived from crude oil are inexpensive feedstock as compared to single molecule liquid or gaseous feedstock. Moreover, liquid hydrocarbons feedstock derived from crude oil does not require further downstream processes like hydroprocessing, alkylation, reforming and cracking. More importantly, liquid hydrocarbon feedstock derived from crude oil is having potential rich of carbon and hydrogen and also with minor amount of intrinsic CNT growth promoter molecules such as hetero atomic molecules. The heterocyclic compounds containing oxygen, nitrogen and sulphur are invariably present in different proportions in crude oil and distillates. In particular, thiophene compounds acts as intrinsic growth promoters for the CNT process. Without being bound by theory, a stable metal-sulphur bond will form with sulphur compounds which cause to preserve and stabilize the active metallic species.

These intrinsic CNT growth promoter molecules are invariably present in crude oil and its derivatives. The presence of intrinsic growth molecules prevents the catalyst agglomeration during the CNT growth process. In the prior art, growth promoter molecules are externally added to the feedstock in controlled manner during the process to enhance the CNT growth. However, adding growth promoter molecules makes the process economically expensive.

The active metals used in accordance with present invention include Group VIII metals, preferably Fe, Co, Ni, whereas the promoters used in accordance with present invention include Group IB, VIB, VIIB and VIII metals, preferably Fe, Ni, Co, Cu, Mo, W, Cr or Mn or mixtures thereof. The metal oxides used in accordance with the present invention include, but are not limited to alumina, silica, silica-alumina, zeolite, titania, magnesia, clay materials and carbon materials.

The composition of active metal component varies from 1 to 100 wt. %/wt. % with respect to the metal oxide support, while the ratio of active metal to promoter varies from 0 to 20 wt. %/wt. %. In a preferred embodiment, ratio of active metal to support is 5-40 wt. %/wt. % with respect to support and ratio of active metal to promoter is 1-10 wt. %/wt. %.

The preparation method according to the present invention comprises feeding of the petroleum crude oil and its derivatives into a catalytic reactor with help of carrier gas; selected from hydrogen, nitrogen, helium, argon and carbon dioxide or mixtures thereof. The feed rate is maintained at residence time of the reactor in the range 1 to 100 minutes. The operating pressure of reactor is maintained at 1 mbar to 10 bar and the reactor temperature is in the range of 500-1200° C. The catalytic reactor is operated either in batch or continuous mode is equipped with or without vibrating function. The said catalytic reactor when operated for catalytic conversion of crude oil and its products limits the surface encapsulation of carbon layer over the catalyst particles; resulting in longer catalytic activity and improved purity of carbon nanotubes.

The reactor flow diagram shown in FIG. 13 is described as below.

(1) and (2) are mass flow controllers for nitrogen and hydrogen gases. The mass flow controllers regulate the desired flow rate of gases as per required process conditions. (3) is the feed tank embedded with feed pump and (4) is the line heater to carry the feed into the pre heater section (5) and (6) are the feed inlet points for the reactor. The catalyst trays (7) and baskets (8) are arranged in series in the reactor as shown in FIG. 13. The catalyst is loaded on each tray of desired volume and feed vapor is in contact with catalyst surface during the process. The catalytic vibrating flow reactor consists of multiple catalyst trays (7) and collecting baskets (8) arranged in series. The CNT is produced in the catalyst tray (7) and is collected in collecting basket (8) through perforated catalyst tray with the help of vibrator. The order of catalyst tray and collecting basket can be interchangeable. The metallic shaft is equipped with electromechanical vibrator (10) operated electrically interim/continuously during the CNT process. The product gases from the reactor pass through heat exchanger (11) and finally reach to wet gas flow meter (13). The gas sample collection is taken from on-off valve (12).

The operation of vibrator during CNT synthesis helps to minimize the surface encapsulation of catalyst particle with growing carbon surface, thereby activity of catalyst maintains longer time as compared with process without operating vibrator. Furthermore, carbon purity also improved significantly as compared with process operating without vibrator. In general, conventional fixed bed reactors suffer from lower catalyst contact area as a result of surface encapsulation of catalyst particles, which leads to the yield of CNT being not satisfactory.

At the end of the process, the reactor is cooled off in inert atmosphere and the product, carbon nanotubes is recovered from the reactor with yield of 1 wt. % to 80 wt. %. The diameter of carbon nanotubes varies from 1 to 100 nm, preferably 1 nm to 30 nm. In addition to the production of carbon nanotubes, the resultant product gas stream generated from the conversion of crude oil and its derivatives comprises of hydrogen and lighter hydrocarbons of C1 to C5 gases along with solid carbon nanotubes. It is also to be noted that CO, $CO_2$ gases are formed in negligible quantities.

In an embodiment of the invention, hydrogen gas is separated from the product gas streams and the remaining byproducts of lighter hydrocarbons recycled back into the reactor partially or completely in order to improve the overall productivity of the carbon nanotubes and hydrogen.

In another embodiment of the present invention, hydrogen and methane are produced simultaneously along with carbon nanotubes, which can be used as transportation fuel wherein the hydrogen is in the range of 10 vol % to 90 vol % of product gas, and methane in the range 10 vol % to 90 vol % of product gas. The hydrogen and methane mix as fuel results in lower emission compared to other fossil fuel based fuel.

The carbon nanotubes produced from this invention have the advantage of being produced directly from petroleum crude oil and its products with purity ranges from 70 wt. % to 99.5 wt. % of product gas, preferably in the range of 90 wt. % to 98 wt. % of product gas. This is a significant advancement over existing art where single molecule gaseous or liquid feedstocks are used in production of carbon nanotubes. Another distinct advantage is that there are no liquid by-products formed during the process, the only products obtained are carbon nanotubes, hydrogen and methane and trace amounts of $C_2$-$C_5$ hydrocarbons, all of which have industrial applicability. The hydrogen yield ranges from 1 wt. % to 12 wt. % of liquid hydrocarbon, preferably 5 wt. % to 10 wt. % of liquid hydrocarbon. The product gas comprises of hydrogen in the range of 10 vol. % to 90 vol. % of product gas and methane in the range of 10 vol. % to 90 vol. % of product gas.

Having described the basic aspects of the present invention, the following non-limiting examples illustrate specific embodiment thereof.

EXAMPLE 1

8 g of alumina supported Fe—Mo catalyst is loaded inside the middle of vibrating reactor. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature of 700° C., hydrogen gas (75 sccm i.e., Standard Cubic Centimeters per Minute) is introduced into the reactor in order to reduce the catalyst and reduction is continued for 4 hrs. After the completion of catalyst reduction, nitrogen gas is introduced at the same temperature. The reduction purpose is to reduce the metal oxide species into metallic species, which is an active phase catalytic species for hydrocarbon decomposition. At this stage, crude oil having low sulphur (<1 wt. % S) is fed into the reactor at a flow rate of 10 g/h with 50 sccm of nitrogen carrier gas and is continued for 450 minutes. The purpose of carrier gas is to carry the feed vapor into the reactor, and also to maintain inert/reduced atmosphere during the CNT process. The product gas stream is further analyzed by refinery gas analyzer. The chromatogram shows yield pattern of gases such as hydrogen, nitrogen, methane and other lighter hydrocarbons. After the completion of run, the reactor is cooled in nitrogen atmosphere and solid carbon nanotubes collected and yield is estimated. Material balance has been calculated on the weight % basis of low sulphur crude oil feed stock on nitrogen free basis and is shown in Table 1.

TABLE 1

Material balance for low sulphur crude oil to carbon nanotube, hydrogen and lighter hydrocarbons

| Input | Weight (%) | Output | Weight (%) |
|---|---|---|---|
| Low Sulphur Crude oil | 100 | Carbon NanoTube | 50.5 |
| | | Hydrogen | 10.8 |
| | | Methane | 27.6 |
| | | C2-C5 | 9.2 |
| | | CO & $CO_2$ | 1.9 |
| Total Feed | 100 | Total Product | 100 |

The carbon nanotube produced has been analysed using Transmission Electron Microscope (TEM) and the image is shown in the FIG. 1. The image shows formation of carbon nanotube with average inner diameter of 5-7 nm and average outer diameter of 15-25 nm. The carbon nanotube produced was analyzed for purity using thermogravimetry and the thermogram is shown in the FIG. 2. The carbon nanotube purity obtained is 89.68 wt. %.

EXAMPLE 2

8 g of alumina supported Fe—Mo catalyst is loaded inside the middle of vibrating reactor. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature of 700° C., hydrogen gas (75 sccm) is introduced into the reactor in order to reduce the catalyst and reduction is continued for 4 hrs. After the completion of catalyst reduction, nitrogen gas is introduced at the same temperature. At this stage, crude oil having sulphur content of >1 wt. % is fed into the reactor at a flow rate of 14 g/h with 50 sccm of nitrogen carrier gas and is continued for 430 min. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and yield is estimated. Material balance has been calculated on the weight % basis of high sulphur crude oil feed stock on nitrogen free basis and is shown in Table 2.

TABLE 2

Material balance for high sulphur crude oil to carbon nanotube, hydrogen and lighter hydrocarbons

| Feed | Weight (%) | Product | Weight (%) |
|---|---|---|---|
| High Sulphur Crude oil | 100 | Carbon NanoTube | 44.5 |
| | | Hydrogen | 9.0 |
| | | Methane | 39.5 |
| | | C2-C5 | 4.0 |
| | | CO & $CO_2$ | 3.0 |
| Total Feed | 100 | Total Product | 100 |

The carbon nanotube produced has been analyzed using Transmission Electron Microscope (TEM) and the image is shown in the FIG. 3. The image shows formation of carbon nanotube with average inner diameter of 5-7 nm and average outer diameter of 10-15 nm. The carbon nanotube produced was analyzed for purity using thermogravimetry and the thermogram is shown in FIG. 4. The carbon nanotube purity obtained is 82.67 wt. %.

EXAMPLE 3

8 g of alumina supported Fe—Mo catalyst is loaded inside the middle of vibrating reactor. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature 700° C., hydrogen gas (75 sccm) is introduced into the reactor in order to reduce the catalyst and reduction is continued for 4 hrs. After the completion of catalyst reduction, reactor temperature is decreased to 600° C. in the nitrogen atmosphere. At this stage, high sulphur crude oil having sulphur content of >1 wt. % is fed into the reactor at a flow rate of 14 g/h with 50 sccm of nitrogen carrier gas and is continued for 430 min. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and yield is estimated. Material balance has been calculated on the weight % basis of high sulphur crude oil feed stock on nitrogen free basis and is shown in Table 3.

TABLE 3

Material balance for high sulphur crude oil to carbon nanotube, hydrogen and lighter hydrocarbons at 600° C.

| Feed | Weight (%) | Product | Weight (%) |
|---|---|---|---|
| High Sulphur Crude oil | 100 | Carbon NanoTube | 37.7 |
| | | Hydrogen | 7.8 |
| | | Methane | 41.2 |
| | | C2-C5 | 11.3 |
| | | CO & $CO_2$ | 2.0 |
| Total Feed | 100 | Total Product | 100 |

The morphology and diameter of resultant carbon nanotube has been analyzed by Transmission Electron Microscope (TEM) and is shown in the FIG. 5. The image shows the formation of carbon nanotube with average inner diameter of 6-8 nm. Further, the purity of as produced carbon nanotube was analyzed by thermogravimetry (TGA). The TGA image shown in FIG. 6 and infers that obtained carbon nanotube purity is 77 wt. %.

EXAMPLE 4

8 g of alumina supported Fe—Mo catalyst is loaded inside the middle of reactor, wherein vibrator function is not operated during the process. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature of 700° C., hydrogen gas (75 sccm) is introduced into the reactor in order to reduce the catalyst and reduction is continued for 4 hrs. After the completion of catalyst reduction, nitrogen gas is introduced at the same temperature. At this stage, naphtha is fed into the reactor at a flow rate of 8.5 g/h with 40 sccm of nitrogen carrier gas and is continued for 566 min. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and yield is estimated. Material balance has been calculated on the weight % basis of naphtha feed stock on nitrogen free basis and is shown in Table 4.

TABLE 4

Material balance for Naphtha to carbon nanotube, hydrogen and lighter hydrocarbons

| Feed | Weight (%) | Product | Weight (%) |
|---|---|---|---|
| Naphtha | 100 | Carbon NanoTube | 51.4 |
| | | Hydrogen | 11.0 |
| | | Methane | 28.7 |
| | | C2-C5 | 6.1 |
| | | CO & $CO_2$ | 2.8 |
| Total Feed | 100 | Total Product | 100 |

The carbon nanotube produced has been analyzed using Transmission Electron Microscope (TEM) and the image is shown in the FIG. 7. The image shows formation of carbon nanotube with average inner diameter of 2-6 nm and outer diameter of 4-20 nm. The carbon nanotube produced was analyzed for purity using thermogravimetry and the thermogram is shown in the FIG. 8. The carbon nanotube purity obtained is 80 wt. %.

EXAMPLE 5

8 g of alumina supported Fe—Mo catalyst is loaded inside the middle of vibrating reactor. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature of 700° C., hydrogen gas (75 sccm) is introduced into the reactor in order to reduce the catalyst and reduction is continued for 4 hrs. After the completion of catalyst reduction, nitrogen gas is introduced at the same temperature. At this stage, naphtha is fed into the reactor at a flow rate of 18.5 g/h with 40 sccm of nitrogen carrier gas and is continued for 395 min. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and yield is estimated. Material balance has been calculated on the weight % basis of naphtha feed stock on nitrogen free basis and is shown in Table 5 (without vibrator) and Table 6 (with vibrator).

TABLE 5

Material balance for Naphtha to carbon nanotube, hydrogen and lighter hydrocarbons (without vibrator operation)

| Feed | Weight (%) | Product | Weight (%) |
|---|---|---|---|
| Naphtha | 100 | Carbon NanoTube | 43.5 |
| | | Hydrogen | 8.3 |
| | | Methane | 35.4 |
| | | C2-C5 | 11.0 |
| | | CO & $CO_2$ | 1.8 |
| Total Feed | 100 | Total Product | 100 |

TABLE 6

Material balance for Naphtha to carbon nanotube, hydrogen and lighter hydrocarbons (with vibrator operation)

| Feed | Weight (%) | Product | Weight (%) |
|---|---|---|---|
| Naphtha | 100 | Carbon NanoTube | 48.6 |
| | | Hydrogen | 9.4 |
| | | Methane | 31.5 |
| | | C2-C5 | 9.0 |
| | | CO & $CO_2$ | 1.5 |
| Total Feed | 100 | Total Product | 100 |

The carbon nanotube produced without vibrator operation has been analyzed using Transmission Electron Microscope (TEM) and the image is shown in the FIG. 9. The image shows formation of carbon nanotube with average inner diameter of 3-6 nm and outer diameter of 4-16 nm. In contrast thereto, TEM of CNT produced with vibrator operation shown in FIG. 11, the diameter of carbon nanotube with average diameter of 3-5 nm and outer diameter of 4-12 nm.

The carbon nanotube produced was analyzed for purity using thermogravimetry and compared with thermogram of carbon nanotubes produced from reactor without operating vibrating function and the comparative thermogram is shown in the FIG. 10.

The purity of carbon nanotube with and without operating vibrating function is shown in FIG. 10, which indicates that carbon nanotube purity is increased to 95 wt. % with vibrator operation, while purity of 88 wt. % is observed without operating vibrating function.

EXAMPLE 6

8 g of alumina supported Fe—Mo catalyst is loaded inside the middle of vibrating reactor. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature of 700° C., hydrogen gas (75 sccm) is introduced into the reactor in order to reduce the catalyst and reduction is continued for 4 hrs. After the completion of catalyst reduction, nitrogen gas introduced at the same temperature. At this stage, light cycle oil (LCO) is fed into the reactor at a flow rate of 5.3 g/h with 40 sccm of nitrogen carrier gas and is continued for 640 min. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and yield is estimated. Material balance has been calculated on the weight % basis of light cycle oil feedstock on nitrogen free basis and is shown in Table 7. In contrast thereto, product gas distribution from light cycle oil on the vol % basis is shown in Table 8.

TABLE 7

Material balance for Light Cycle Oil to carbon nanotube, hydrogen and lighter hydrocarbons

| Feed | Weight (%) | Product | Weight (%) |
|---|---|---|---|
| Light Cycle oil | 100 | Carbon NanoTube | 61.6 |
| | | Hydrogen | 10.0 |
| | | Methane | 19.0 |
| | | C2-C5 | 7.3 |
| | | CO & $CO_2$ | 2.1 |
| Total Feed | 100 | Total Product | 100 |

TABLE 8

Product gas yield distribution from light cycle oil on vol % basis (From gas chromatography):

| Feed | Product gas | Vol. (%) |
|---|---|---|
| Light Cycle oil | Hydrogen | 86.2 |
| | Methane | 12.8 |
| | C2-C5 | 0.8 |
| | CO & $CO_2$ | 0.2 |
| | Total Product | 100 |

Figure 12:
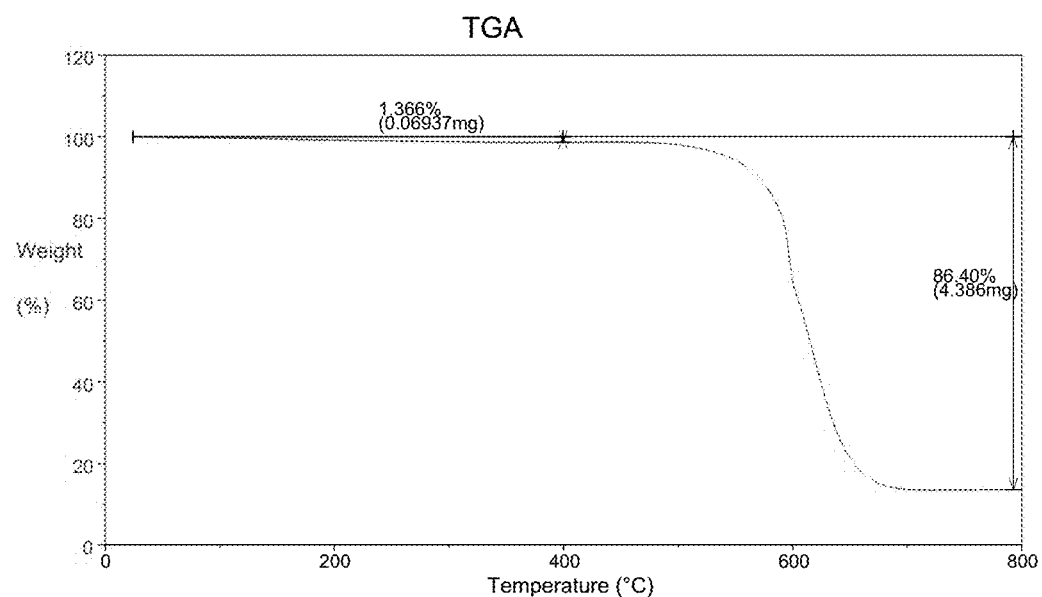

The carbon nanotube produced has been analyzed using Transmission Electron Microscope (TEM) and the image is shown in the FIG. 12. The image shows formation of carbon nanotube with average inner diameter of 5-7 nm and outer diameter of 20-25 nm. The carbon nanotube produced was analyzed for purity using thermogravimetry and the thermogram is shown in the FIG. 13. The carbon nanotube purity obtained is 86.4 wt. %.

EXAMPLE 7

8 g of alumina supported Fe—Mo catalyst is loaded inside the middle of vibrating reactor. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature of 700° C., hydrogen gas is introduced into the reactor in order to reduce the catalyst and reduction is continued for 4 hrs. After the completion of catalyst reduction, nitrogen gas introduced at the same temperature. At this stage, crude oil having high sulphur (>1 wt. % S) is fed into the reactor at a flow rate of 10 g/h with nitrogen carrier gas and is continued for 450 minutes. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and yield is estimated. Material balance has been calculated on the weight % basis of high sulphur crude oil feed stock on nitrogen free basis and is shown in Table 9.

TABLE 9

Material balance for high sulphur crude oil to carbon nanotube, hydrogen and lighter hydrocarbons

| Input | Weight (%) | Output | Weight (%) |
|---|---|---|---|
| High Sulphur Crude oil | 100 | Carbon NanoTube | 53.1 |
| | | Hydrogen | 10.9 |
| | | Methane | 25.3 |
| | | C2-C5 | 9.0 |
| | | CO & $CO_2$ | 1.7 |
| Total Feed | 100 | Total Product | 100 |

The carbon nanotube produced has been analyzed using Transmission Electron Microscope (TEM) and it shows formation of carbon nanotube with average inner diameter of 5-7 nm and average outer diameter of 15-25 nm. The purity of carbon nanotube is analyzed by thermo gravimetry and is obtained as 93% (FIG. 14).

EXAMPLE 8

8 g of alumina supported Fe—Mo catalyst is loaded inside the middle of vibrating reactor. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature of 700° C., hydrogen gas is introduced into the reactor in order to reduce the catalyst and reduction is continued for 4 hrs. After the completion of catalyst reduction, nitrogen gas introduced at 500° C. At this stage, naphtha is fed into the reactor at a flow rate of 18.5 g/h with nitrogen carrier gas and it is continued for 395 minutes. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and yield is estimated. Material balance has been calculated on the weight % basis of naphtha feed stock on nitrogen free basis and is shown in Table 10.

TABLE 10

Material balance for Naphtha at reaction temperature 500° C. to carbon nanotube, hydrogen and lighter hydrocarbons

| Feed | Weight (%) | Product | Weight (%) |
|---|---|---|---|
| Naphtha | 100 | Carbon Nanotube | 7.0 |
| | | Hydrogen | 2.9 |
| | | Methane | 56.7 |
| | | C2-C5+ | 31.6 |
| | | CO & $CO_2$ | 1.8 |
| Total Feed | 100 | Total Product | 100 |

The carbon nanotube produced has been analyzed using Transmission Electron Microscope (TEM) and it shows formation of carbon nanotube with average inner diameter of 3-6 nm and outer diameter of 4-16 nm. The TGA plot (FIG. 15) represents the purity of carbon is around 53 wt. %.

EXAMPLE 9

8 g of alumina supported Fe—Mo catalyst is loaded inside the middle of vibrating reactor. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature of 700° C., hydrogen gas is introduced into the reactor in order to reduce the catalyst and reduction is continued for 4 hrs. After the completion of catalyst reduction, nitrogen gas is introduced at 600° C. At this stage, naphtha is fed into the reactor at a flow rate of 18.5 g/h with nitrogen carrier gas and is continued for 395 min. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and yield is estimated. Material balance has been calculated on the weight % basis of naphtha feed stock on nitrogen free basis and is shown in Table 11.

TABLE 11

Material balance for Naphtha at reaction temperature 600° C. to carbon nanotube, hydrogen and lighter hydrocarbons

| Feed | Weight (%) | Product | Weight (%) |
|---|---|---|---|
| Naphtha | 100 | Carbon Nanotube | 23.2 |
| | | Hydrogen | 6.0 |
| | | Methane | 43.4 |
| | | C2-C5 | 25.7 |
| | | CO & $CO_2$ | 1.7 |
| Total Feed | 100 | Total Product | 100 |

The carbon nanotube produced has been analyzed using Transmission Electron Microscope (TEM) and it shows formation of carbon nanotube with average inner diameter of 3-6 nm and outer diameter of 4-16 nm. The TGA plot shown below represents the carbon purity is 72 wt. % (FIG. 16).

As temperature increases, the kinetic energy of gas diffusion into the catalyst particle increased, which lead to increased CNT growth.

EXAMPLE 10

8 g of alumina supported Ni—Co catalyst is loaded inside the middle of vibrating reactor. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature of 700° C., hydrogen gas is introduced into the reactor in order to reduce the catalyst and reduction is continued for 4 hrs. After the completion of catalyst reduction, nitrogen gas is introduced at 700° C. At this stage, naphtha is fed into the reactor at a flow rate of 18.5 g/h with nitrogen carrier gas and is continued for 395 min. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and yield is estimated. Material balance has been calculated on the weight % basis of naphtha feed stock on nitrogen free basis and is shown in Table 12.

TABLE 12

Material balance for Naphtha at reaction temperature 700° C. to carbon nanotube, hydrogen and lighter hydrocarbons

| Feed | Weight (%) | Product | Weight (%) |
|---|---|---|---|
| Naphtha | 100 | Carbon Nanotube | 38.64 |
| | | Hydrogen | 8.52 |
| | | Methane | 43.89 |
| | | C2-C5 | 7.61 |
| | | CO & $CO_2$ | 1.34 |
| Total Feed | 100 | Total Product | 100 |

The carbon nanotube produced has been analyzed using Transmission Electron Microscope (TEM) and it shows formation of carbon nanotube with average outer diameter of 10-30 nm.

The purity of carbon nanotube is determined by TGA, and is estimated as 85 wt. % (FIG. 17).

EXAMPLE 11

8 g of alumina supported Ni—Co catalyst is loaded inside the middle of vibrating reactor. The flow rate of carrier and reducing gases are controlled through the electronic mass flow meters and temperature of catalyst and reactor is measured through the thermocouple. Further catalyst is heated up to 500° C., in presence of nitrogen carrier gas. After attaining the desired temperature of 500° C., hydrogen gas is introduced into the reactor in order to reduce the catalyst and reduction is continued for 4 hrs. After the completion of catalyst reduction, nitrogen gas is introduced at 500° C. At this stage, naphtha is fed into the reactor at a flow rate of 18.5 g/h with nitrogen carrier gas and is continued for 395 min. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and yield is estimated. Material balance has been calculated on the weight % basis of naphtha feed stock on nitrogen free basis and is shown in Table 13.

TABLE 13

Material balance for Naphtha at reaction temperature 500° C. to carbon nanotube, hydrogen and lighter hydrocarbons

| Feed | Weight (%) | Product | Weight (%) |
|---|---|---|---|
| Naphtha | 100 | Carbon Nanotube | 14.28 |
| | | Hydrogen | 3.38 |
| | | $CH_4$, C2-C5 & CO, $CO_2$ | 82.34 |
| Total Feed | 100 | Total Product | 100 |

The carbon nanotube produced has been analyzed using Transmission Electron Microscope (TEM) and it shows formation of carbon nanotube with average outer diameter of 10-30 nm.

The purity of carbon nanotube produced with Ni—Co catalyst at 500° C. is shown in FIG. 18, and is estimated as 66 wt. %.

Both examples 10 and 11 refer to CNT process conditions and reduction temperatures kept same and data has been provided at two different temperatures i.e. 500° C. and 700° C. for Ni—Co catalysts. In example 11, reduction is performed at lower temperature and reaction also is performed at the same temperature.

EXAMPLE 12

8 g of alumina supported Fe—Mo catalyst is loaded inside the middle of vibrating reactor. The flow rate of carrier and reducing gases are controlled through the electronic mass flow meters and temperature of catalyst and reactor is measured through the thermocouple. Further catalyst is heated up to 700° C., in presence of nitrogen carrier gas. After attaining the desired temperature of 700° C., hydrogen gas (75 sccm) is introduced into the reactor in order to reduce the catalyst and reduction is continued for 4 hrs. After the completion of catalyst reduction, naphtha is fed into the reactor at a flow rate of 18.5 g/h with 40 sccm of hydrogen as carrier gas and is continued for 395 min. The product gas stream is further analyzed by refinery gas analyzer. The chromatogram shows yield pattern of gases such as hydrogen, methane and other lighter hydrocarbons. After the completion of run, reactor is cooled in nitrogen atmosphere and solid carbon nanotubes collected and then yield is estimated. Material balance has been calculated on the weight % basis of naphtha feed stock on nitrogen free basis and is shown in Table 14.

TABLE 14

Material balance for Naphtha to carbon nanotube, hydrogen and lighter hydrocarbons

| Feed | Weight (%) | Product | Weight (%) |
|---|---|---|---|
| Naphtha | 100 | Carbon NanoTube | 46.4 |
| | | Hydrogen | 9.2 |
| | | Methane | 33.1 |
| | | C2-C5 | 9.7 |
| | | CO & $CO_2$ | 1.6 |
| Total Feed | 100 | Total Product | 100 |

The carbon nanotube produced above has been analyzed using Transmission Electron Microscope (TEM) and the image is shown in FIG. 19. The image shows formation of carbon nanotube with average inner diameter of 7-10 nm and outer diameter of 15-25 nm. The carbon nanotube produced was analyzed for purity using thermogravimetry and the thermogram is shown in the FIG. 20. The carbon nanotube purity obtained is 84.3 wt. %.

EXAMPLE 13

8 g of alumina supported Fe—Mo catalyst is loaded inside the middle of vibrating reactor. The flow rate of carrier and reducing gases is controlled through the electronic mass flow meters and temperature of catalyst and reactor is measured through the thermocouple. Further catalyst is heated up to 800° C., in presence of nitrogen carrier gas. After attaining the desired temperature of 800° C., hydrogen gas (75 sccm) is introduced into the reactor in order to reduce the catalyst and reduction is continued for 4 hrs. After the completion of catalyst reduction, naphtha is fed into the reactor at a flow rate of 18.5 g/h with 40 sccm of hydrogen as carrier gas and is continued for 395 min. The product gas stream is further analyzed by refinery gas analyzer. The chromatogram shows yield pattern of gases such as hydrogen, nitrogen, methane and other lighter hydrocarbons. After the completion of run, reactor is cooled in nitrogen atmosphere and solid carbon nanotubes collected and then yield is estimated. Material balance has been calculated on the weight % basis of naphtha feed stock on nitrogen free basis and is shown in Table 15.

TABLE 15

Material balance for Naphtha to carbon nanotube, hydrogen and lighter hydrocarbons at 800° C.

| Feed | Weight (%) | Product | Weight (%) |
|---|---|---|---|
| Naphtha | 100 | Carbon NanoTube | 51.7 |
| | | Hydrogen | 8.8 |
| | | Methane | 28.5 |
| | | C2-C5 | 9.6 |
| | | CO & $CO_2$ | 1.4 |
| Total Feed | 100 | Total Product | 100 |

The carbon nanotube produced above has been analyzed using Transmission Electron Microscope (TEM) and the image is shown in FIG. 21. The image shows formation of carbon nanotube with average inner diameter of 3-7 nm and outer diameter of 10-20 nm. The carbon nanotube produced was analyzed for purity using thermogravimetry and the thermogram is shown in FIG. 22. The carbon nanotube purity obtained is 91.5 wt. %.

Both the examples refers that CNT process condition and reduction temperatures kept same and data has been provided at two different temperatures i.e. 500° C. and 700° C.) for Ni—Co catalysts. In example 11, reduction is performed at lower temperature and reaction is also performed at the same temperature.

We claim:

1. A process for the simultaneous production of carbon nanotubes and product gas comprising hydrogen and lighter hydrocarbons, from a petroleum crude oil or its products or mixtures thereof, comprising:
    feeding the petroleum crude oil or its products or mixtures thereof, in a vibrating reactor operated with vibrating function; and
    converting the petroleum crude oil or its products or mixtures thereof, having heteroatomic intrinsic growth promotors with a catalyst for simultaneous production of the carbon nanotubes, hydrogen and lighter hydrocarbons; wherein,
    the petroleum crude oil or its products or mixtures thereof, comprises at least one of naphtha, light cycle oil, decanted clarified oil from fluid catalytic cracking, aromatic extract, unconverted oil from hydrocracker bottom, deasphalted oil, coker furnace oil, pyrolysis furnace oil, reduced crude oil, or vacuum gas oil; and
    output products comprising carbon nanotubes having purity ranges from 70 wt % to 99.5 wt %; and
    product gas comprising of $C_1$ to $C_5$ lighter hydrocarbons which mainly consists of methane, ethane, ethylene, propane, propylene, butane, isobutane, 2-butene and pentane, is in the range of 10 vol. % to 90 vol. %; wherein, methane composition is in the range of 10 vol. % to 90 vol. % of the product gas.

2. The process of claim 1, wherein the catalyst is bulk or supported active metal catalyst, with or without promoter.

3. The process of claim 2, wherein the active metal is supported on a metal oxide support and the metal oxide is selected from the group comprising of alumina, silica, silica-alumina, zeolite, titania, magnesia, clay materials.

4. The process of claim 2, wherein ratio of active metal to metal oxide support is in the range of 1 to 100 wt. %/wt. % and the ratio of active metal to promoter is in the range of 0 to 20 wt. %/wt. %.

5. The process of claim 2, wherein ratio of active metal to support is in the range of 5-40 wt. %/wt. % and ratio of active metal to promoter is in the range of 1-10 wt. %/wt. %.

6. The process of claim 2, wherein the active metal is selected from Group VIII metals and the promoter is selected from Group IB, VIB, VIIB, VIII metals.

7. The process of claim 6, wherein the active metal is selected from the group comprising of Fe, Co, Ni and the promoter is selected from the group comprising of Fe, Ni Co, Cu, Mo, W, Cr or Mn.

8. The process of claim 1, wherein the heteroatomic intrinsic growth promotors are sulphur and nitrogen containing molecules.

9. The process of claim 1, wherein the temperature of the vibrating reactor is maintained in the range of 300-1200° C.

10. The process of claim 1, wherein the temperature of the vibrating reactor is maintained in the range of 500-900° C.

11. The process of claim 1, wherein the vibrating reactor is maintained at an operating pressure in the range of 1 mbar to 10 bar.

12. The process of claim 1, wherein the vibrating reactor is maintained at an operating pressure in the range of 1 mbar to 5 bar.

13. The process of claim 1, wherein catalytic conversion is carried out at an elevated temperature in the range of 500-1200° C.

14. The process of claim 1, wherein feeding of the petroleum crude oil or its products or mixtures thereof, into the vibrating reactor is carried out with help of a carrier gas and the carrier gas comprises nitrogen, helium, argon, hydrogen, carbon dioxide, or mixture thereof.

15. The process of claim 1, wherein the carbon nanotube yield ranges from from 1 wt. % to 80 wt. % of the petroleum crude oil or its products or mixtures thereof.

16. The process of claim 1, wherein the carbon nanotube purity ranges from 90 wt. % to 98 wt. %.

17. The process of claim 1, wherein the yield of product gas comprising hydrogen and lighter hydrocarbons is in the range of 10 vol. % to 90 vol. %.

18. The process of claim 1, wherein the yield of hydrogen is in the range of 1 wt. % to 12 wt. % of the petroleum crude oil or its products or mixtures thereof.

19. The process of claim 1, wherein the product gas stream comprising $C_1$ to $C_5$ hydrocarbons is partially or completely recycled back into the vibrating reactor or as feed to another vibrating reactor.

20. The process of claim 1, wherein the carbon nanotubes are produced with diameter of 1 to 100 nm.

* * * * *